United States Patent [19]
Benaron et al.

[11] Patent Number: 5,769,791
[45] Date of Patent: *Jun. 23, 1998

[54] TISSUE INTERROGATING DEVICE AND METHODS

[75] Inventors: David A. Benaron, Redwood City, Calif.; Daniel S. Goldberger, Boulder, Colo.; David E. Goodman, San Francisco; Robert S. Smith, Berkeley, both of Calif.

[73] Assignee: Sextant Medical Corporation, Boulder, Colo.

[ * ] Notice: The term of this patent shall not extend beyond the expiration date of Pat. No. 5,460,182.

[21] Appl. No.: 472,863

[22] Filed: Jun. 7, 1995

Related U.S. Application Data

[63] Continuation of Ser. No. 437,327, May 9, 1995, which is a continuation-in-part of Ser. No. 944,516, Sep. 14, 1992, Pat. No. 5,460,182, which is a continuation-in-part of Ser. No. 24,278, Feb. 26, 1993.

[51] Int. Cl.$^6$ .................................................... A61B 6/00
[52] U.S. Cl. ............................................ 600/473; 600/476
[58] Field of Search ..................................... 128/664, 665, 128/633, 634, 754; 606/2, 14, 15, 167, 172, 173, 170, 16, 205, 211, 207, 139, 140; 607/88, 89; 356/432, 433, 435; 433/29, 31; 600/473, 476, 310, 342, 567

[56] References Cited

U.S. PATENT DOCUMENTS

| | | | |
|---|---|---|---|
| 2,437,916 | 3/1948 | Greenwald | 128/2 |
| 3,674,008 | 7/1972 | Johnson | 128/665 |
| 3,847,483 | 11/1974 | Shaw et al. | 356/41 |
| 3,941,121 | 3/1976 | Olinger et al. | 128/6 |

(List continued on next page.)

FOREIGN PATENT DOCUMENTS

| | | | |
|---|---|---|---|
| 0 017 108 | 10/1992 | WIPO | 128/634 |

OTHER PUBLICATIONS

J.S. Wyatt et al., "Measurement of Optical Path Length for Cerebral Near–Infrared Spectroscopy in Newborn Infants", *Dev Neurosci* 1990; 12:140–144.

Howard Mark, Chemometrics In Near–Infrared Spectroscopy, Analytica Chimica Act, 223 (1989), pp. 75–93.

D. Benaron et al., "Non–Invasive Estimation of Cerebral Oxygenation and Oxygen Consumption Using Phase–Shift Spectrophotometry", Proceedings of the Twelfth Annual International Conference of the IEEE Engineering in Medicine and Biology Society, vol. 12: No. 5, 1990, pp. 2004–2006.

(List continued on next page.)

*Primary Examiner*—Brian L. Casler
*Attorney, Agent, or Firm*—Orrick, Herrington & Sutcliffe

[57] ABSTRACT

A tool for nondestructive interrogation of the tissue including a light source emitter and detector which may be mounted directly on the surgical tool in a tissue contacting surface for interrogation or mounted remotely and guided to the surgical field with fiber optic cables. The light source may be broadband and wavelength differentiation can be accomplished at the detector via filters or gratings, or using time, frequency, or space resolved methods. Alternatively, n discrete monochromatic light sources may be provided which are subsequently multiplexed into a single detector by time or by frequency multiplexing. The optical sensing elements can be built into a surgical tool end effector tip such as a tissue grasping tool which has cooperating jaws (bivalve or multi-element). In the preferred embodiment the light source (or the fiber optic guide) is mounted on one jaw and the detector (or fiber optic guide) is mounted in the opposing jaw so that the light emitter and detector are facing one another either directly (i.e., on the same optical axis when the tool is closed) or acutely (i.e., with intersecting optical axes so that the light emitted is detected). In this case, the sensor is working in a transmission modality. Arrangements with the optical components mounted on the same member of a single member or a multi member structure, operating in a reflective modality, are disclosed.

53 Claims, 11 Drawing Sheets

U.S. PATENT DOCUMENTS

| | | | |
|---|---|---|---|
| 3,961,621 | 6/1976 | Northeved | 128/2 B |
| 3,963,019 | 6/1976 | Quandt | 128/2 T |
| 4,085,756 | 4/1978 | Weaver | 128/303.17 |
| 4,191,191 | 3/1980 | Auburn | 128/347 |
| 4,269,192 | 5/1981 | Matsuo | 128/665 |
| 4,290,433 | 9/1981 | Alfano | 128/665 |
| 4,295,470 | 10/1981 | Shaw et al. | 128/634 |
| 4,299,230 | 11/1981 | Kubota | 128/630 |
| 4,311,138 | 1/1982 | Sugarman | 128/214.4 |
| 4,322,164 | 3/1982 | Shaw et al. | 356/243 |
| 4,350,148 | 9/1982 | Sivak, Jr. et al. | 128/4 |
| 4,356,682 | 11/1982 | Kubota | 128/630 |
| 4,380,240 | 4/1983 | Jobsis | 128/633 |
| 4,410,020 | 10/1983 | Lorenz | 141/65 |
| 4,416,285 | 11/1983 | Shaw et al. | 128/634 |
| 4,421,106 | 12/1983 | Uehara | 128/4 |
| 4,448,194 | 5/1984 | DiGiovanni et al. | 128/334 R |
| 4,471,781 | 9/1984 | DiGiovanni et al. | 128/334 R |
| 4,502,487 | 3/1985 | Dubrucq et al. | 128/665 |
| 4,509,368 | 4/1985 | Whiting | 73/624 |
| 4,515,165 | 5/1985 | Carroll | 128/664 |
| 4,527,569 | 7/1985 | Kolb | 128/660 |
| 4,532,935 | 8/1985 | Wang | 128/753 |
| 4,539,586 | 9/1985 | Danna et al. | 358/98 |
| 4,555,179 | 11/1985 | Langerhole et al. | 356/237 |
| 4,566,438 | 1/1986 | Liese et al. | 128/6 |
| 4,601,710 | 7/1986 | Moll | 604/165 |
| 4,617,940 | 10/1986 | Wang | 128/753 |
| 4,622,974 | 11/1986 | Coleman et al. | 128/634 |
| 4,633,885 | 1/1987 | DuBrucq | 128/736 |
| 4,650,327 | 3/1987 | Ogi | 356/243 |
| 4,658,825 | 4/1987 | Hochberg et al. | 128/634 |
| 4,667,229 | 5/1987 | Cooper et al. | 358/9 |
| 4,682,585 | 7/1987 | Hilterbrandt | 128/4 |
| 4,763,662 | 8/1988 | Yokoi | 128/660 |
| 4,765,736 | 8/1988 | Gallagher | 356/300 |
| 4,773,097 | 9/1988 | Suzaki | 382/6 |
| 4,805,623 | 2/1989 | Jobsis | 128/633 |
| 4,810,875 | 3/1989 | Wyatt | 128/665 |
| 4,854,320 | 8/1989 | Dew et al. | 128/397 |
| 4,864,648 | 9/1989 | Kordts et al. | 455/608 |
| 4,872,187 | 10/1989 | Nakahata | 378/4 |
| 4,887,606 | 12/1989 | Yock et al. | 128/662.05 |
| 4,902,280 | 2/1990 | Lander | 604/165 |
| 4,910,404 | 3/1990 | Cho | 250/358 |
| 4,911,148 | 3/1990 | Sosnowaki et al. | 128/6 |
| 4,917,097 | 4/1990 | Proudian et al. | 128/662.06 |
| 4,930,516 | 6/1990 | Alfano et al. | 128/665 |
| 4,945,895 | 8/1990 | Takai et al. | 128/6 |
| 4,948,974 | 8/1990 | Nelson et al. | 128/664 |
| 4,951,677 | 8/1990 | Crowley et al. | 128/662.06 |
| 4,959,063 | 9/1990 | Kojima | 606/15 |
| 4,970,757 | 11/1990 | Heiland et al. | 452/140 |
| 4,972,827 | 11/1990 | Kishi et al. | 128/3 |
| 4,998,527 | 3/1991 | Meyer | 128/6 |
| 5,000,752 | 3/1991 | Hoskin et al. | 606/9 |
| 5,002,051 | 3/1991 | Dew et al. | 128/395 |
| 5,002,557 | 3/1991 | Hasson | 606/191 |
| 5,030,206 | 7/1991 | Lander | 604/164 |
| 5,030,207 | 7/1991 | Mersch et al. | 604/168 |
| 5,037,433 | 8/1991 | Wilk et al. | 606/139 |
| 5,053,016 | 10/1991 | Lander | 604/69 |
| 5,057,695 | 10/1991 | Hirao et al. | 250/575 |
| 5,066,288 | 11/1991 | Deniega et al. | 604/274 |
| 5,070,874 | 12/1991 | Barnes et al. | 128/664 |
| 5,078,712 | 1/1992 | Easley et al. | 606/16 |
| 5,088,493 | 2/1992 | Giannini et al. | 128/664 |
| 5,099,123 | 3/1992 | Harjunmaa | 250/339 |
| 5,100,402 | 3/1992 | Fan | 606/41 |
| 5,104,382 | 4/1992 | Brickerhoff et al. | 604/165 |
| 5,104,383 | 4/1992 | Shichman | 604/167 |
| 5,112,330 | 5/1992 | Nishigaki et al. | 606/46 |
| 5,114,407 | 5/1992 | Burbank | 604/164 |
| 5,116,353 | 5/1992 | Green | 606/184 |
| 5,119,815 | 6/1992 | Chance | 128/633 |
| 5,131,398 | 7/1992 | Alfano et al. | 128/665 |
| 5,137,355 | 8/1992 | Barbour et al. | 356/342 |
| 5,139,025 | 8/1992 | Lewis et al. | 128/665 |
| 5,140,984 | 8/1992 | Dew et al. | 128/395 |
| 5,140,989 | 8/1992 | Lewis et al. | 128/665 |
| 5,152,278 | 10/1992 | Clayman | 128/4 |
| 5,154,709 | 10/1992 | Johnson | 606/45 |
| 5,186,714 | 2/1993 | Boudreault et al. | 604/21 |
| 5,192,280 | 3/1993 | Parins | 606/48 |
| 5,197,964 | 3/1993 | Parins | 606/48 |
| 5,201,732 | 4/1993 | Parins et al. | 606/47 |
| 5,203,339 | 4/1993 | Knuttel et al. | 128/665 |
| 5,213,105 | 5/1993 | Gratton et al. | 250/341 |
| 5,217,458 | 6/1993 | Parins | 606/48 |
| 5,219,345 | 6/1993 | Potter | 128/665 |
| 5,250,047 | 10/1993 | Rydell | 606/48 |
| 5,258,006 | 11/1993 | Rydell et al. | 606/205 |
| 5,271,380 | 12/1993 | Riek et al. | 128/4 |
| 5,275,168 | 1/1994 | Reintjes et al. | 128/665 |
| 5,280,788 | 1/1994 | Janes et al. | 128/665 |
| 5,290,278 | 3/1994 | Anderson | 606/15 |
| 5,290,286 | 3/1994 | Parins | 606/50 |
| 5,300,065 | 4/1994 | Anderson | 606/13 |
| 5,318,023 | 6/1994 | Vari et al. | 128/634 |
| 5,324,289 | 6/1994 | Eggers | 606/48 |
| 5,330,471 | 7/1994 | Eggers | 606/48 |
| 5,352,222 | 10/1994 | Rydell | 606/37 |
| 5,352,223 | 10/1994 | McBrayer et al. | 606/51 |

OTHER PUBLICATIONS

D. Benaron et al., "Optical Path Length of 754nm and 816nm Light Emitted Into the Head of Infants", Proceedings of the Twelfth Annual International Conference of the IEEE Engineering in Medicine and Biology Society, vol. 12., No. 3, 1990, pp. 117–119.

D. Benaron et al., "Tomographic Time–of–Flight Optical Imaging Scanner with Non–Parallel Ray Geometry, Non––Parallel Rotational Optical Tomography", *Applied Optics* (in press) pp. 2–33.

Nezhat et al., "Laparoscopic Removal of Dermoid Cysts", *Obstetrics & Gynecology*, vol. 73, No. 2, Feb. 1989, pp. 278–280.

Nezhat et al., "Laparoscopic radical hysterectomy with paraaortic and pelvic node dissection", *Am J Obstet Gynecol* 1992, 166:864–5.

Nezhat et al., "Salpingectomy via Laparoscopy, A New Surgical Approach", *Journal of Laparoendoscopic Surgery*, vol. 1, No. 2, 1991, pp. 91–95.

Nezhat et al., "Endoscopic Infertility Surgery", *The Journal of Reproductive Medicine*, vol. 34, No. 2, Feb. 1989, pp. 127–134.

Nezhat et al., "Videolaseroscopy For Oophorectomy", *Am J Obstet Gynecol* 1991, 165:1323–30.

Nezhat et al., "Laparoscopic Versus Abdominal Hysterectomy", *The Journal of Reproductive Medicine*, Vo. 37, No. 3, Mar. 1992, pp. 247–250.

Nezhat et al., "Videolaseroscopy", *Obstetrics And Gynecology Clinics of North America*, vol. 18, No. 3, Sep. 1991, pp. 585–604.

Nezhat et al., "Operative Laparoscopy (Minimally Invasive Surgery), State of the Art", *J. Gynecol Surg.*, 8:111, 1992, pp. 111–141.

Benaron, "2D and 3D Images of Thick Tissue . . . ", SPIE 1641: 35–45 (1992).

Benaron, "Imaging (NIRI) and quantitation (NIRS) In Tissue . . . ", SPIE 1888: 10–21, Jan. (1993).

Benaron et al., "Optical Time–Of–Flight and Absorbance Imaging Of Biologic Medic", *Science*, (1993) 259: 1463–6.

Edholm et al., "Tissue Identification During Needle Puncture By Reflection Spectrophotometry", Med & Biol Engng, vol. 6, pp. 409–413 (1968).

Talamini et al., "Laproscopic Equipment and Instrumentation", Chapter 2, Surgical Laparoscopy (Zucker ed), (1991) pp. 23–27, 35–36, 40–55.

"Instrumentation" Laparoscopic Complication (1991) pp. 5–13.

Edholm et al., "Detection of Aortic Atheromatosis In Vivo By Reflection Spectrophotometry", J. Atheroscler, Res. 5, (1965).

Polanyi In Vivo Oximeter With Fast Dynamic Response, The Review of Scientific Instruments, vol. 33, No. 10, 1962, pp. 1050–1054.

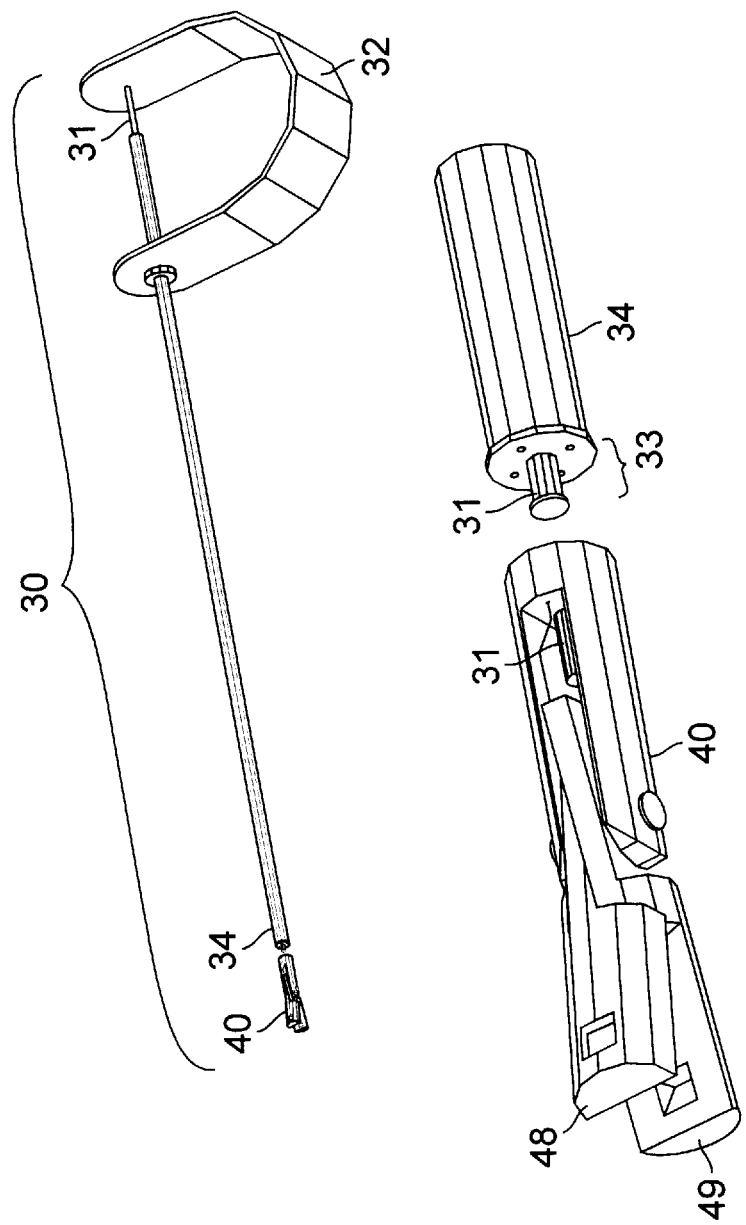

| | ABDOM WALL | FAT | LIVER | GALL BLADDER | BOWEL | BLADDER | URETER | UTERINE WALL | DIAPHR | SMALL BOWEL | COLON | FAT | ARTERY |
|---|---|---|---|---|---|---|---|---|---|---|---|---|---|
| | PROBE | PROBE | PROBE | PROBE | PROBE | PROBE | PROBE | PROBE | PROBE | PROBE | PROBE | PROBE | PROBE |
| ABDOMINAL WALL | 2 | | | | | | | | | | | | |
| FAT | | 2 | | | | | | | | | | | |
| LIVER | | | 2 | | | | | | | | | | 1 |
| GALL BLADDER | | | | 2 | | | | | | | | | |
| BOWEL | | | | | 0 | | | | | | | | |
| BLADDER | | | | | | 0 | 1 | | | | | | |
| URETER | | | | | 1 | | 2 | 2 | 1 | 1 | | | |
| UTERINE WALL | | | | | | | | 4 | | | | | |
| DIAPHRAGM | | | | | | | | | 2 | | | | |
| SMALL BOWEL | | | | | | | | | | 3 | | | |
| COLON | | | | | | | 1 | | | | 2 | | |
| FAT | | | | | | | | | | | | 2 | |
| ARTERY | | | | | | | | | | | | | 2 |
| VEIN | | | | | | | | | | | | | |
| GANGLIA | | | | | | | | 1 | 1 | | | | |
| BONEY PELVIS | | | | | | | | | | | | | |
| ARTERY (GRASPER) | | | | | | | | | | | | | |
| VEIN (GRASPER) | | | | | | | | | | | | | |
| URETER (GRASPER) | | | | | | | | | | | | | |
| LIVER (GRASPER) | | | | | | | | | | | | | |
| GALL BLADDER (GRASPER) | | | | | | | | | | | | | |
| LIVER (GRASPER) | | | | | | | | | 2 | | | | |
| BILE DUCT (GRASPER) | | | | | | | | | | | | | |

63 DETERMINATIONS
15 FALSE POS/FALSE NEG

FIG. 11A

| | VEIN PROBE | GANGLI PROBE | BONEY PELVIS PROBE | ARTERY GRASPER | VEIN GRASPER | URETER GRASPER | LIVER GRASPER | GALL BLADDER GRASPER | LIVER GRASPER | BILE DUCT GRASPER |
|---|---|---|---|---|---|---|---|---|---|---|
| ABDOMINAL WALL | | | | | | | | | | |
| FAT | | | | | | | | | | |
| LIVER | | | | | | | | | | |
| GALL BLADDER | | | | | | | | | | |
| BOWEL | | | | | | | | | | |
| BLADDER | | | | | | | | | | |
| URETER | | | | | | | | | | |
| UTERINE WALL | | | | | | | | | | |
| DIAPHRAGM | | | | | | | | | | |
| SMALL BOWEL | 1 | | | | | | | | | |
| COLON | | | | 1 | | | | | | |
| FAT | | | | | | | | | | |
| ARTERY | 2 | | | | | | | | | |
| VEIN | | 1 | | | | | | | | |
| GANGLIA | | | 3 | | | | | | | |
| BONEY PELVIS | | | | 2 | 2 | | | | | |
| ARTERY (GRASPER) | | | | | | 4 | | | | |
| VEIN (GRASPER) | | | | | | | | | | |
| URETER (GRASPER) | | | | | | | 2 | | | |
| LIVER (GRASPER) | | | | | | | | 2 | | |
| GALL BLADDER (GRASPER) | | | | | | | | | 0 | |
| LIVER (GRASPER) | | | | | | | | | | |
| BILE DUCT (GRASPER) | | | | | | | | | | 4 |

FIG. 11B

TISSUE INTERROGATING DEVICE AND METHODS

RELATED APPLICATIONS

This application is a continuation of U.S. patent application Ser. No. 08/437,327, filed May 9, 1995 in the names of Daniel S. Goldberger and Robert S. Smith and entitled SURGICAL TOOL END EFFECTOR, which is copending and commonly assigned, which is a continuation-in-part of U.S. patent application Ser. No. 07/944,516 filed Sep. 14, 1992, now U.S. Pat. No. 5,460,182 in the names of David E. Goodman and Daniel S. Goldberger and entitled TISSUE PENETRATING APPARATUS AND METHODS, which is copending and commonly owned, and a continuation-in-part of U.S. patent application Ser. No. 08/024,278 filed Feb. 26, 1993 in the name of David A. Benaron and entitled DEVICE AND METHOD FOR DETECTION, LOCALIZATION, AND CHARACTERIZATION OF INHOMOGENEITIES IN TURBID MEDIA, which is copending, and which applications are expressly incorporated herein by reference in their entireties.

FIELD OF THE INVENTION

The present invention relates to sensors for in vivo measurements of body tissues, more particularly to surgical tools and instruments capable of non-destructive interrogation of body tissues during surgical and/or diagnostic procedures.

BACKGROUND OF THE INVENTION

In the context of this specification, the terms "interrogate" and "interrogation" refer to the act and the process of determining a characteristic of one or more of the structure, function and composition of an in vivo sample of body tissue. The term "non-destructive" refers to a determination of the characteristic, or more than one characteristic, by analysis of a portion of tissue, perhaps without having to penetrate into the tissue portion that is to be analyzed, and hence includes both non-invasive and touching contact, notwithstanding that the interrogation occurs using a member that may have penetrated into or through (i.e., is invasive to) some other tissue portion that is not the in vivo tissue portion to be interrogated.

The field of minimally invasive surgery has recently experienced dramatic growth. Laparoscopic appendectomy, cholecystectomy (removal of the gall bladder) and various gynecological procedures have become widely adopted in clinical practice. When performed safely, the minimally invasive alternatives to traditional surgical intervention can reduce costs of care by shortening hospital stays and recuperation times. They also provide additional benefits such as reduced patient discomfort and better cosmetic results, i.e., reduced scarring.

In traditional surgery, the patient's skin is cut along a length and retracted. The surgeon has a large open field in which to operate. In minimally invasive surgery, a portal is formed in the patient's skin and tools are inserted into the body cavity. For example, in laparoscopic surgery, a rigid laparoscope is passed through the portal. The laparoscope provides direct visualization inside the body cavity, typically using a miniature video camera attached to the eyepiece. Although the body cavity (and subsequent procedures) can be easily viewed on a video screen (CRT), the surgeon cannot physically touch and feel the tissues. This deprives the surgeon of a vitally important cue in helping him to determine the tissue composition, and whether the procedure can be safely performed or should be modified or terminated. For example, it can be very difficult for the surgeon to identify blood vessels, such as arteries, on a video display without being able to feel directly the tissue bed containing the arteries. It also can be difficult to distinguish vital structures, such as the bile ducts of the liver and gall bladder, lymph ducts, ureters, and nerves from the surrounding tissues. In addition, it can be difficult to distinguish visually abnormal tissue for the removal of pathological lesions, e.g., tumors, from vital structures and vessels. Inadvertent ablation, puncture or cutting of these tissue structures can result in significant complications. In severe cases it may require major (traditional) surgical intervention to repair the damage.

The tools that surgeons are using on patients, for example, the surgical knife, suture, and staples, have not changed significantly since their inception. The alternate techniques for surgical intervention, such as endoscopy, electrosurgical or hemostatic cutting and coagulation, laser welding, cryosurgery, and other thermal techniques which have been developed, depend on the surgeons' skill in applying those techniques. As a result, the skill set of the surgeon is often of critical importance in the surgical procedure applied, and the successful outcome of the surgical intervention. When the intervention is performed during minimally invasive surgery, the surgeon's skill level is even more important.

It has been suggested to provide an aid to the surgeon to facilitate the surgical procedure. In this regard, prior techniques are known for distinguishing pathological lesions from the surrounding healthy tissues. One technique is direct biopsy with microscopical analysis during surgery. The problems with the biopsy method include that it is invasive, in that tissue samples are required, and slow, in that time is required for transporting and processing the tissue sample for analysis. These delays are costly and potentially hazardous, as there is increasing patient risk as time under anesthesia increases.

U.S. Pat. Nos. 5,131,398, 4,416,285, and others refer to using optics and needles or catheters, for distinguishing cancer from noncancerous tissue, or analyzing the content of fluids. International publication WO 92/17108 and U.S. Pat. No. 5,280,7880, refer to analyzing tissue in an existing state to determine whether a tissue is or is not metastatic cancer, or to diagnose an existing condition of tissue.

Other devices using optics and fiber optics for in vivo measurement of biological fluids and tissues are known. U.S. Pat. Nos. 4,633,885 and 4,502,487 refer to an optical thermodetector for in vivo testing of tissue which contains both temperature and color sensors in a probe or needle-like extension. U.S. Pat. No. 4,311,138 refers to an illuminated hypodermic needle to help guide its placement into a blood vessel. U.S. Pat. No. 5,030,207 describes an intravenous needle with a fiber optic for showing the instantaneous entry into a vein.

Patel, et al., *J. Vasc. Surg.*, Vol. 8, No. 3, pp. 346–8 (1988), refers to an optical catheter used to cannulate and identify the course of the saphenous vein during heart surgery. U.S. Pat. No. 4,658,825 describes a combined spiral EKG electrode and fiber optic pH probe for use in monitoring a fetus during labor. U.S. Pat. No. 4,622,974 refers to a fiber optic needle with a sample cavity assembly for making in-vivo measurement of chemical concentrations in the body, wherein fluids are aspirated into the sample cavity where light absorption measurements are made. U.S. Pat. No. 4,945,895 refers to a small caliber fiber optic bundle disposed through a pre-positioned needle lumen for making direct observations of tissues. U.S. Pat. No. 4,566,438 refers to a fiber-optic stylet for a surgical or diagnostic type needle that is used for determining the area in which the needle is positioned within the body during a diagnostic or surgical procedure. Edholm, et al., *Med & Biol. Engrg.*, Vol. 6, pp. 409–13 (1968), refers to a fiber optic needle for tissue identification by reflection spectroscopy. U.S. Pat. Nos. 4,269,192, 4,410,020 and 4,556,438 refer to placing optical fibers into a needle or syringe to report on the location of the tool or device as it is placed into the tissue.

A problem with the invasive devices referred to in the foregoing references is that penetration of the tissue under interrogation is required. This act can create complications, such as tissue trauma and hemorrhage. Bleeding not only can be dangerous to the patient, but it can also disturb the proper visualization of tissue structures during laparoscopic-type (endoscopic) procedures, making the procedure more difficult and more time consuming.

Some non-invasive optical tissue interrogation devices are also known. Pulse oximeters are widely used to monitor the blood oxygen saturation and pulse rate of patients. They utilize optical sensors, typically placed on a finger, nose or earlobe, to make measurements of blood constituents. See for example, U.S. Pat. No. 4,830,014. U.S. Pat. No. 4,938,218 refers to an exemplary perinatal pulse oximeter sensor for monitoring a fetus during labor. One problem with these non-invasive devices is that they require sustained sensor contact with well perfused epidermal skin, without expressing venous blood, over long periods of time to monitor effectively blood oxygen saturation and pulse rate. Another problem is that they adjust the light intensity of multiple light frequencies for the tissue interrogation to obtain a signal that is insensitive to variations of tissue color (pigment), hair or other surface phenomenon and surface configuration from interrogation to interrogation. Another problem with these devices is that, without some mechanism for maintaining the sensor in good touching contact against the tissue without affecting the normal perfusion of the tissue, which is itself difficult to achieve, they do not operate well over time.

Notwithstanding the foregoing devices and procedures, there remains a need for improved sensors and tools for non-destructive interrogation of tissue during invasive and minimally invasive diagnostic and surgical procedures. Indeed, no such known tool has been successfully commercialized.

SUMMARY OF THE INVENTION

It is an object of the present invention to provide instruments for interrogating tissue non-destructively for use during minimally invasive surgical procedures.

It is another object of the invention to provide a surgeon with an instrument that can interrogate a number of different selected sample areas of tissue inside a body cavity, particularly during minimally invasive surgical procedures. It is another object to provide cues to compensate for the surgeon's inability to touch and feel, and in some cases see, tissues directly during minimally invasive surgical procedures.

It is another object of the invention to interrogate tissue during minimally invasive tissue intervention procedures and generate an alarm signal to indicate either a likely desired or an undesired result of the intervention based on the interrogation, e.g., the presence of one of a number of particular types or kinds of tissue or vital structures or vascularized tissue.

Broadly, the present invention is directed to methods and apparatus coupling surgical tools with optical sensors for non-destructively interrogating tissue to discriminate tissue types based on the spectral characteristics of the tissue in response to one or more wavelengths of radiation passed into the tissue. Preferably, an instrument (tool) and method in accordance with the present invention can distinguish vital organs and vital tissues. More preferably, the invention identifies the tissue being interrogated, for example, as presenting one or more of blood vessels (veins and arteries), urine containing structures (ureter and bladder), bile containing structures, nerve tissue (ganglia), lymph containing structures, inflamed tissue, fat, diseased tissue, endometrial tissue (lining of the uterus), as well as certain tissue, e.g., abdominal wall, and the tissue types of internal organs and structures, e.g., liver, pancreas, lung, kidneys, gall bladder, bony pelvis, colon, small bowels, diaphragm, etc.

In an alternate embodiment the invention also concerns sensing the temperature of tissue to be operated on during minimally invasive procedures, and identifying a characteristic of the sensed tissue in response to the sensed temperature. Thus, both spectral characteristics and temperature can be used to discriminate and identify the tissue.

Another aspect of the invention concerns an end effector tip (hereinafter a "tip") which includes, on the one hand, optical components for interrogating tissue, and on the other hand, a structure for performing a selected surgical intervention procedure. More specifically, each tip is preferably a detachable component of a surgical intervention tool, and is replaceable and interchangeable as between tools, and also may have a disposable or reusable construction.

In accordance with one such aspect of the invention, a surgical instrument is provided having a probe member for contacting tissue and a plurality of optical components disposed on the member, for example, for non-destructive interrogation of tissue proximate to the member during a surgical intervention or other interrogation procedure. The member may be configured with a tip that is one of a single body probe, having a blunt edge or a cutting edge (or both), or a multibody probe having two or more cooperating elements. The multibody probe may be a bi-valve structure having two lever elements cooperatively hinged together, a structure having two tissue contacting elements cooperatively arranged for grasping or cutting or more than two tissue contacting elements operating in cooperation.

Preferably, the plurality of optical components include one or more optical emitting windows through which light emitted by a light source is launched to illuminate tissue, and one or more optical detecting windows through which the light illumination in response to the launched emitted light is coupled and detected or sensed by a light detector. The emitted light may be at one or more discrete wavelengths or a broadband light source or a combination of broadband and discrete wavelengths. When one optical emitting window or one optical detecting window is used, more than one wavelength may be launched using a plurality of discrete light sources, e.g., light emitting diodes ("LED") and synchronous or frequency multiplexing techniques, or using a broadband light source such as a Xenon or filament lamp, e.g., a krypton gas filled bulb, together with one or more light conducting waveguides. The plurality of wavelengths are similarly coupled by the one optical detecting window and then demultiplexed into the desired wavelengths of the spectral characterization which are sensed by one or more photodetectors. The same multiplexing and demultiplexing may be used when more than one optical window is used for launching and/or coupling. The sensed wavelengths may be one or more of the wavelengths emitted by the light emitting element and/or a wavelength emitted from the tissue in response to the emitted light, e.g., a fluorescent wavelength. Filters, gratings or other optical elements and one or more photodetectors may be used for sensing the selected wavelengths from the coupled light.

The optical emitting and detecting windows may be fiber optic materials having suitably polished ends for launching and coupling light to and from the tissue. The fiber ends are preferably mounted on the member in one of any number of arrangements so that the light does not pass directly from the emitting fiber to the detecting fiber, but, rather, passes through the tissue to be interrogated. Other optical elements, such as prisms, mirrors, light integrating spheres or wells, may also be used to facilitate light launching and coupling, more specifically, transmission through the tissue.

The terms "element" and "windows" are used herein in connection with the launching and coupling (detection) of electromagnetic radiation, which terms are defined to include, without limitation, optical elements and optical windows which are capable of launching and coupling optical wavelengths of electromagnetic wavelengths, as well as non optical wavelengths.

Another aspect of the present invention concerns a surgical instrument having a first tissue contacting member and a second tissue contacting member and containing a plurality of optical components for non-destructively interrogating body tissues interposed between the first and second members during surgical or other procedures. The light path may be transmissive in that it passes from one member through the tissue to the other member or it may be reflective in that it passes from an emitting window on one member into the tissue and is reflected back to a cooperating detecting window on the same member (or a different member). A combination of reflective and transmissive operation also may be used. In addition, temporal variation of the emitted light intensity, such as phase-modulation or time-of-flight analysis, both known in the study of tissue optics, can be used to help separate out the effects of absorbance and scattering. Additionally, emitted and detected light can be measured at different points in space, and this can allow a similar separation of absorbance and scatter, or even generation of an image using the surgical tool. These techniques are well-known to those skilled in the art of tissue optics, and therefore are not described in detail herein. See, e.g., *Medical Optical Tomography: Functional Imaging & Monitoring*, G. Muller et al., Published by SPIE-The International Society of Optical Engineering; 1993; and D.A. Benaron et al., "Optical Time of Flight and Absorbance Imaging of Biologic Media," *Science* 259:1463–6 (1993). However, their incorporation into tissue interrogating invasive and surgical tools is deemed within the scope of this invention. In any event, the light wavelengths launched into the tissue are transmitted, absorbed, remitted, and reflected and cause fluorescence in varying degrees by the tissue. The variations produce a light illumination at the detecting window (and coupled to the detector) that differs from the illumination launched, and thus indicates the spectral nature of the tissue illuminated. The coupled illumination is sensed and processed to identify the spectral characteristics, i.e., composition, structure and/or function, of the tissue being interrogated.

Preferably, the plurality of optical components include one or more optical emitting windows on one member and one or more optical detecting windows facing a tissue contacting surface of the other member such that the optical emitting and detecting windows couple well and pass light through the tissue. As noted, the optical emitting and detecting windows may be lengths of fiber optic materials having polished ends in the tissue contacting surfaces and associated light sources and light detectors.

The surgical instruments or "tools" may be any instrument adapted to contact, grasp or sever tissue. They include, without limitation: forceps, scissors, knives, staplers, clip appliers, and other like devices; probes, suction probes, and irrigation probes; and tissue penetrating devices such as insufflation devices, biopsy needles, trocars and the like. Tools of a known construction may be adapted, by incorporation of the optical elements and analysis functions, for use in the present invention.

Another aspect of the present invention is directed to examining the time-varying light intensity of the sensed light to determine whether pulsations are present. Pulsations of one type would be seen when interrogating tissue having an artery in or proximate to the tissue bed. Pulsations of a different type would be seen when interrogating tissue having a vein in the tissue bed. In one embodiment, the interrogating tool also may be provided with a grasping mechanism to induce pulses on the tissue and monitor the tissue response. For example, a bi-valve structure having two contacting members that are pneumatically operated to compress tissue can induce pulses. Optical elements located in the members then can sense the tissue response.

Another aspect of the present invention is directed to analyzing the spectral characteristics of the coupled light from the tissue under interrogation in order to determine the probable composition and structure of the tissue. The sensed spectral characteristics at a selected number of wavelengths may be compared to a library containing stored spectral records which represent the spectral characteristic components corresponding to various known types of tissue and structures in the body. A probable tissue type is then identified based on a correlation between the detected and stored spectral characteristics. The correlation may be a match or a best match or based on a K Nearest Neighbors (KNN) or Soft Independent Modeling of Class Analogy (SIMCA) algorithm, as found in the Pirouette Multivariate data analysis for IBM PC systems, available from Infometrix, Seattle WA, or some other matching routine.

Another aspect of the present invention is directed to interposing the two members of the surgical instrument between body tissues (or vise versa) for the purpose of illuminating the tissue with one or more wavelengths of radiation from the optical emitter and measuring the intensity and spectral characteristics of the coupled light at the optical detector.

Another aspect of the present invention is directed to a surgical instrument having a member for contacting tissue and a temperature sensing device on the contacting member. This provides for measuring the temperature of a tissue bed in contact with the conducting member. Preferably, the instrument has a second tissue contacting member so that the temperature of the tissue interposed between the contacting members, e.g., two jaws of a surgical forceps, can be monitored. The temperature sensor can be a contacting sensor, a proximity infrared temperature sensor or other temperature sensing device.

In a preferred embodiment, the plurality of optical components, and optionally the temperature sensor, are disposed on the electrodes of a bipolar electrocautery unit or on the opposing blades of an instrument such as forceps, a heated cutting instrument, hemostatic scissors or electrosurgical scissors or along the cutting edge of a scalpel or a tissue penetrating device.

The present invention also is directed to processing the optical signals derived from the optical component to alert the operator, prior to the engagement of a surgical tool for performing a surgical intervention, that the tissue interposed between the instrument "jaws" contains a substantial artery, vein, bile duct or nerve tissue or other tissue type which is not the subject of the intended surgical intervention. This aspect is particularly applicable to tools, such as an electrosurgical unit, a cutting instrument, a stapling or clip applying unit, where the intervention is to be performed on tissue that cannot be directly visualized or felt, and is below the surface of the tissue that can be seen.

Advantageously, the present invention provides an intelligent surgical tool to assist the surgeon in navigating the tool through the healthy tissue and around the tissue that is not the object of the surgical intervention, to reach the tissue that is to be treated. In so doing, the tools provide feedback, in the form of cues and/or alarms, to aid the surgeon in the procedure. These aids result in reducing damage to the healthy tissue, and avoiding complications arising from inadvertent (and heretofore unavoidable) intervention of other tissue types. In addition, the present invention also permits the surgeon to operate more quickly and effectively. This results in further advantages to the patient, whether in major invasive or minimally invasive procedure. As applicants have realized, much more time in surgery is spent navigating through healthy tissue to get to the site requiring intervention and/or treatment, than in determining whether a particular tissue is healthy or abnormal. Hence, the tools of the present invention are particularly directed to distinguishing tissue types to aid the surgeon in this navigation process.

Another advantage of the present invention is that a library of spectral records for appropriate tissue types can be constructed to identify the various types of tissue and organs that are likely to be confronted during a given tissue intervention. As applicants have realized, the variation in the spectral characteristics of a given tissue type or structure vary from one person to the next. However, as compared to the spectral characteristics of different tissue types or structures, those variations tend to remain within a typical range such that each given tissue type has a range of spectral characteristics that is identifiably different from the ranges of the other tissue types. This permits obtaining spectral characteristics over a broad spectrum for different tissues, selecting certain ones of discrete wavelengths from the spectrum, by which the tissue structures and tissue types of interest differ, and classifying tissue types by selected ranges of spectral characteristics that are unique for the different tissue types, e.g., for bile duct, urine containing structures, blood containing structures (arterial and venous), lymph containing structure, nerve tissue, muscle, fat, tissue exudate, inflammatory substances, drugs, toxins, metabolites, tumors, organs, air, water and other body components. As another example, fluorescently tagged monoclonal antibodies selectively absorbed by particular tissue structures can be used to locate that tissue based on the fluorescent property. Also, the introduction of fluids having unique spectral characteristics into a tissue structure, e.g., a gastrointestinal duct, or a kidney, also can be considered in identifying such tissue or structure. Radioisotopes, chemiluminescent, electrochemiluminescent and magnetizable particulate tags that are selectively absorbed or adsorbed can be similarly used.

In a preferred embodiment, the surgical instruments supporting the plurality of optical components are designed to pass through a laparoscopic surgery portal or an endoscope, although the invention is not limited to such surgical instruments.

Preferably, the surgical instruments containing the optical components, more specifically the tips, are disposable in order to insure optimal performance for each type of interrogation as well as to minimize the possibility of cross-contamination.

BRIEF DESCRIPTION OF THE DRAWINGS

Further features of the invention, its nature and various advantages will be more apparent from the accompanying drawings and following detailed description of the invention, in which like reference numerals refer to like elements, and in which:

FIG. 3 is an elevated perspective view of a generic detachable tip for use with the tool of FIG. 1;

FIG. 11 (A and B) are a table of experimental results of tissue identification using a prototype tool in accordance with the present invention.

DETAILED DESCRIPTION OF THE INVENTION

Figure 1:
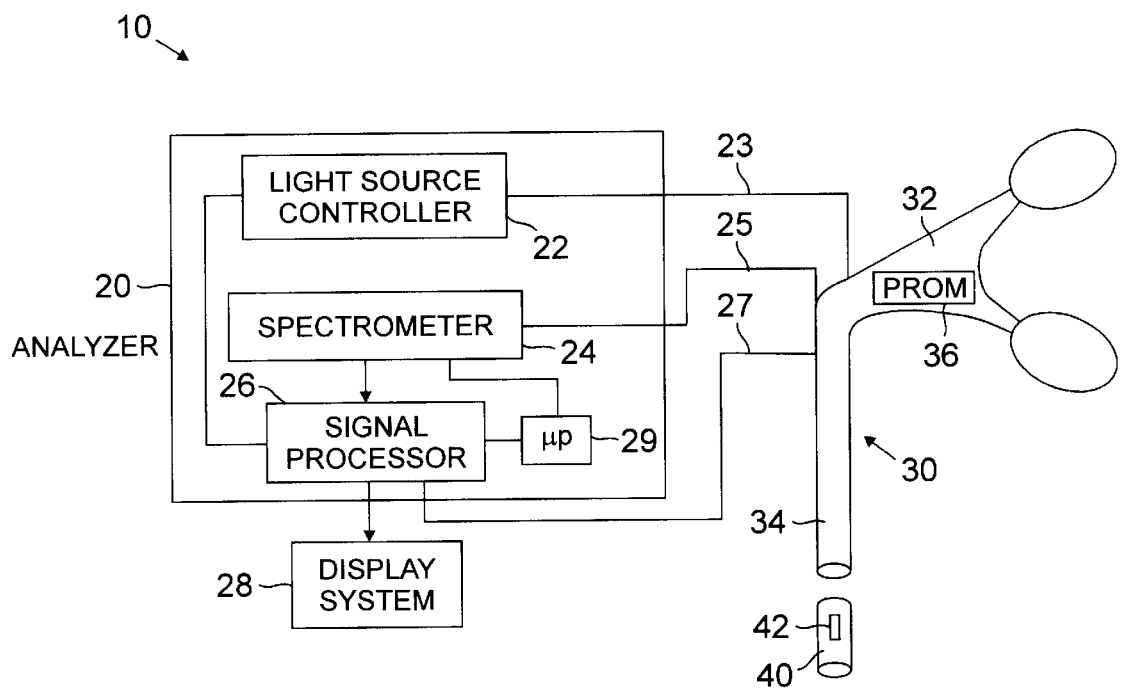
FIG. 1 is a block diagram of a tissue interrogator tool in accordance with a preferred embodiment of the present invention.
Figure 2:
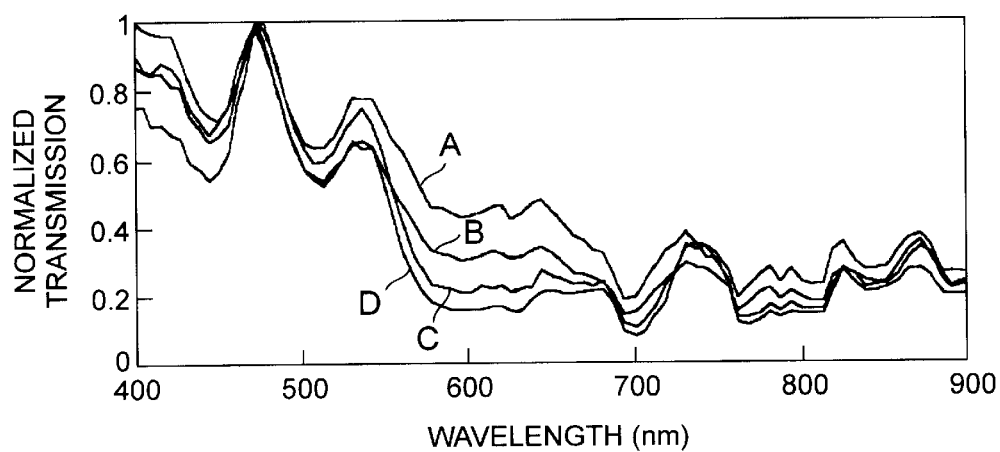
FIG. 2 is a plot of a normalized transmission versus wavelength of light (nm) of four tissue types collected in-vivo using a device in accordance with the present invention.

Referring to FIGS. 1, 2, and 3, a preferred embodiment of the present invention is shown in a generic tool configuration. An interrogation tool 10 includes an analyzer 20 coupled to a surgical tool 30. The optical elements for emitting and detecting light, which are not shown in FIG. 1 for purposes of clarity, may be a part of analyzer 20, tool 30, a tool tip 40, a separate optical probe structure, or some combination of the foregoing. These variations within the scope of the invention will be discussed in more detail separately with respect to FIGS. 3, 3A–3J and 4A–4C.

Referring to FIG. 1, analyzer 20 includes a light source controller 22, a spectrometer 24, a signal processor 26, and a display system 28. These elements are all controllably interconnected and operated under the control of a suitable state control machine, such as a microprocessor 29 executing software instructions.

The light source controller 22 provides a light control signal or signals on path 23 that control the generation of the light to be emitted by a light source and launched into the tissue. The light control signal thus can be suitable to operate a single light source (broadband or discrete), a plurality of discrete light sources (e.g., with a synchronous or frequency multiplexer where appropriate) or both. The light source can be in the tool, i.e., physically inside, or merely coupled to the end of the tool using, e.g., fibers.

Spectrometer 24 receives signals corresponding to the detected light on path 25, performs a color analysis and ascertains the desired spectral characteristics of the detected light, and provides the spectral data to the signal processor 26.

The signal processor 26 receives the determined spectral characteristic data, and, using predetermined algorithms, evaluates the data to identify the type of tissue interrogated. Signal processor 26 provides the determined result to display system 28.

In a preferred embodiment, signal processor 26 also outputs an interlock control signal (illustrated by signal path 27) to tool 30. The interlock control signal is used by tool 30 in its operation. For example, the interlock control signal may be used to disable or enable the tool, override an attempted operation of the tool, interrupt an ongoing operation of the tool (e.g., in response to signal processor 26 identifying an undesired tissue type), or modify tool operating conditions if a desired tissue characteristic is identified (e.g., locating a blood vessel to be coagulated or determining that coagulation is complete). The interlock control signal may be used by tool 30 in a manual response, semiautomatic control, or full automatic control, depending on the nature of the operation performed by the tool and the preferences of the surgeon. These operating parameters may be programmable or determined by manual adjustment of a switch on tool 30 or analyzer 20.

Signal processor 26 (typically considered together with microcomputer 29) controls operation of the analyzer 20 to cause light to be emitted, to detect the coupled light and determine the spectral characteristics of the detected light, and to process the spectral characteristics to characterize the tissue, i.e., to identify the tissue by applying one or more algorithms to the spectral data until the data is determined to correspond to a known tissue type. Microprocessor 29 performs various housekeeping, system management, diagnostic, and data storage and processing functions common to microcomputer—microprocessor controlled devices. This includes functions of the system such as are typical with microprocessor based devices, e.g., signal conditioning, digitization, communications, data storage and compilation, and control. Preferably, microprocessor 29 is a part of signal processor 26 (i.e., the functionalities of each exist within the same software controlled device). The functions of signal processor 26 also may include various circuits for signal conditioning and processing in addition to hardware and software for digital data processing. It should be understood however, that microprocessor 29 could be replaced with solid state circuits, or a separate computer/microcontroller that is coupled to the analyzer 20.

The display system 28 may include one or more of text messages, audible indicators, and visual indicators mounted in a convenient location to be seen. The text messages may be displayed on an LCD type or other stand alone monitor associated with the analyzer 20 and/or on the surgeon's video monitor used to conduct the surgical procedure, e.g., the video monitor of an endoscope. Audible messages may be tones of selected frequency and/or pitch, volume and duty cycle to identify the intended message. Steady state and variable signals may be used. Visual indicators may be a light panel with predetermined locations and/or colors assigned to represent different information.

The surgical tool 30 includes a handle 32, a shaft 34, and a detachable tip 40. The handle 32 represents the controls for the manipulation and operation of the tool in accordance with the conventional manner. This includes manipulating the tool into and inside body tissue or a body cavity, as in the case of a tool for minimally invasive surgery, as well as the surgical procedure to be performed by the tools. The shaft 34 is for passing the distal end of the tool 30 and the tip 40 into tissue, for example, through a portal and through or around internal body tissue in the case of minimally invasive surgery. The handle 32 also contains the usual electronics, switches, fluids, valves, cables, levers, tubes, imaging equipment (in the case of endoscopes, laparoscopes and the like), signal paths, and other mechanisms, circuits, and/or logic for operating the tool to perform its intended functions. Such tools are known in the art. See, e.g., U.S. Pat. Nos. 5,192,280, 3,197,964, 5,201,732, 5,201,732, 5, 217,458, 5,250,047, 5,258,006, 5,290,286, 5,324,289, 5,330,471, 5,352,222 and 5,352,223.

For grasping tools, handles typically include a scissor-like or pistol grip for moving a cable or wire 31 to actuate a moving member 48 relative to an opposing member 49 (see FIG. 3). The opposing member may be fixed or movable, depending on the grasping mechanism.

In accordance with the present invention, the tool may be modified to receive the interlock control signal from signal processor 26 and to respond to the information content of the interlock control signal in an appropriate manner. Such modifications are believed to be within the abilities of a person skilled in the art.

Tip 40 contains the optical emitting and detecting windows for launching light into the tissue and for coupling light after having passed through the tissue to be interrogated, and an end effector structure for performing the surgical procedure on the tissue, as will be described in more detail below with reference to FIGS. 3, 3A–3J, and 4A–4C. Tip 40 is preferably detachable from tool 30 and operatively interconnects with the distal end of tool shaft 34 (see FIG. 3) so that tool 30 can control the tip 40 to perform its intended tissue interrogation and surgical intervention functions. Preferably, tool 30 is constructed with a common fitting 33 at distal end 34 to interfit detachably with more than one type of tip 40, wherein each tip 40 thus has a corresponding fitting to interconnect operatively with distal end 34. As a result, the same tool 30 can control a variety of structurally different tips 40 performing the same or different interrogation and/or intervention functions. In one construction of the invention analyzer 20 may be integrated into tool 30 to provide a single tool 10 with a plurality of useful tips 40.

In operation, the system implemented by tool 10, however constructed, operates light source controller 22 to produce a control signal that causes a light source (not shown in FIG. 1) to emit light, so that light is launched into the tissue being interrogated at tip 40. In addition, it operates spectrometer 24 to collect the detected light (i.e., the light coupled at tip 40 after having passed through the tissue) at the wavelengths of interest and calculate the transmission spectra of the interrogated tissue. Further, it operates signal processor 26 to process the spectral data determined by spectrometer 24 using one or more predetermined classification algorithms to determine the characteristic of the tissue being interrogated, and preferably to identify the tissue. The resultant tissue characteristic or the tissue identification (with a confidence limit) or both can then be displayed on a display system 28. The inability to identify a matching tissue type also is considered an "identification," and an appropriate signal is displayed. More preferably, the interlock control signal may be provided on signal path 27, which signal is responsive to the identification of the interrogated tissue, as described herein.

The present invention also contemplates the use of an interrogator analyzer 20 with any of a number of surgical tools 30. In this case, each tool 30 is preferably provided with an information element 36 that can be read by analyzer 20 for recognizing the type of tool and its operational characteristics. More preferably, the information element 36 is a memory device such as a programmable read only memory ("PROM") device or the like (EEPROM, flash memory, one or two dimensional bar code, coded resistor values, etc.), which contains appropriate use data and calibration information for the specific tool or a key word descriptor for the same. In this regard, different tools 30 will likely require some calibration. The calibration factors thus can be determined, e.g., at the factory, and recorded in the information element 36 for access by analyzer 20, e.g., by signal path 27. The calibration information also can include structure information, e.g., how big are the components of the tip 40 end effector, for performing the surgical intervention procedure. In view of the spectral characteristics, for example, a pair of jaws having a large space between optical elements would likely respond differently from a unipolar electrocautery device or even a retractor. Providing this information to the analyzer 20 (directly or by a key descriptor and an associated look-up table of parameters) permits adjusting the response to the acquired transmission spectra accordingly.

In addition, analyzer 20 also can monitor the operating state of tool 30 during operation using signal path 27, so that it can provide suitable alarms and warnings, and produce an interlock control signal, based on a protocol of the procedure and the determined characteristic(s) of the tissue being interrogated. For example, the analyzer 20 may detect when the surgeon operates a switch to cause electrocautery cutting of tissue, and acts, for one example, to prevent cutting through tissue characterized as a bile duct by disabling the response (electrical and/or mechanical) of the tool to the activation of the trigger switch, and for another example to reduce power when the blood vessel is sufficiently coagulated so as to prevent char from forming. In this context, it is contemplated that the feedback/interlock feature of the analyzer can be overridden and/or disabled by the surgeon as a matter of choice. It should be understood that path 27 can be constructed of a plurality of signal paths, rather than a single path.

Figure 3A:
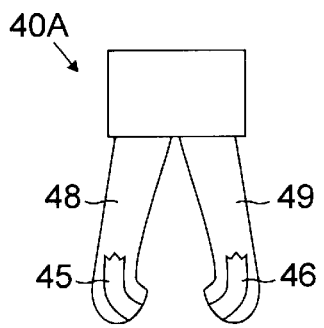
FIGS. 3A–3J are illustrations of various tip configurations for use with the interrogator tool of FIG. 1.
Figure 3B:
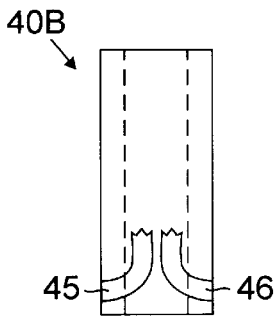
Figure 3C:
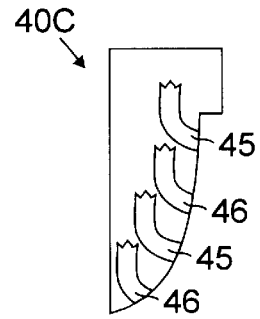
Figure 3D:
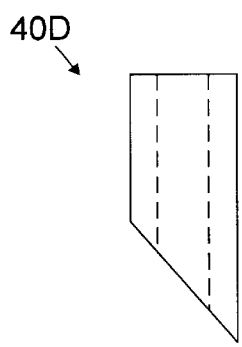
Figure 3E:
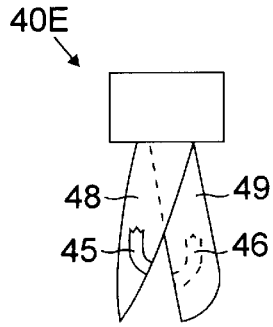
Figure 3F:
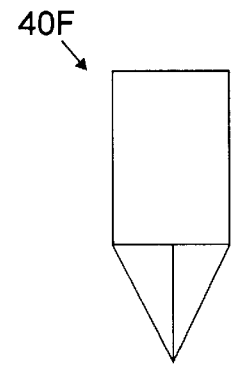
Figure 3G:
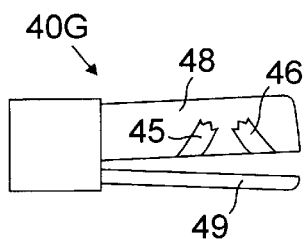
Figure 3I:
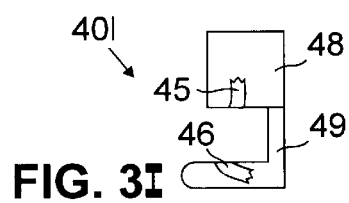
Figure 3H:
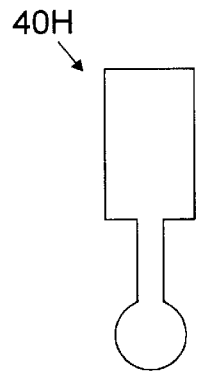
Figure 3J:
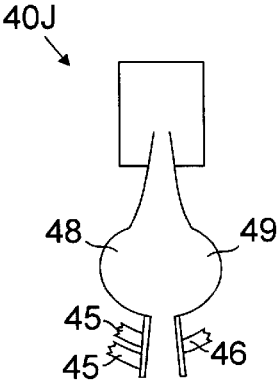

Referring to FIGS. 1, 3, and 3A–3J, detachable tip 40 may be configured as any surgical tool end effector incorporating optical elements and coupling to a male or female fitting (generically shown as 33) on tool distal end 34, as illustrated in FIG. 3. It should be understood that FIGS. 3A–3J are shown generically, and thus may represent more than one type or kind of end effector tips as discussed herein. These structures include, for example: a grasping mechanism (FIGS. 3, 3A, 3I, 3J) such as tongs, retractor, or a clamp; a bi-valve scissors (FIG. 3E) or a two member scissors or clamp (FIG. 3I); a suction or an irrigation probe (FIGS. 3B, 3D); an electrocautery tool, unipolar (FIG. 3H) or bipolar with electrodes on a single contacting surface (FIGS. 3C, 3H), a bi-valve structure (FIGS. 3, 3A, 3E) or other two member structure (FIG. 3J, viewing the two members as movable and fixed); a hemostatic tool that is thermally regulated or autoregulated (FIGS. 3, 3A, 3C, 3E, 3H); a tissue penetrating device such as a needle (FIG. 3D) or a trocar (FIG. 3F); and a surgical stapler or clip applier (FIG. 3G).

The detachable tip 40 is coupled to the shaft 34 at the distal end by a conventional mechanical interconnection 33 that securely engages the two parts (and preferably can be remotely coupled and decoupled at handle 32) and provides for the necessary optical, electrical and mechanical interconnections as appropriate for the given structure and function of the tip 40. It should be understood that the dimensions of tip 40 (and any of tips 40A through 40J) can be selected for use in major surgical intervention, wherein the patient is opened up, minimally invasive surgical intervention, wherein a portal is formed in the patent and the tools all pass through one or more ports, and other endoscopic or exploratory procedures. Portals for minimally invasive surgery are typically 5 mm, 10 mm, or 12 mm in diameter. It also should be understood that light can shine through plastic staples (and clips) to permit monitoring stapling as it occurs, with the staples themselves forming an optical conduit—such that the light is measured at the tip of the staples as they pass through tissue. In addition, light can enter the body from the outside and be detected by an internal tool with detection fiber, such that the light is launched from a different device than the light devicing device. For example, a needle can contain a light source, while another tool, e.g., another needle or one of the aforementioned end effector tools, contains a light coupling fiber connected to a detector.

Each tip 40 also may contain an information element 42 (FIG. 1) which identifies the end effector structure of the tip 40, and may contain any calibration information (or code) necessary for the tip 40, which information element 42 can be interrogated and read by analyzer 20 (or tool 30 depending on the configuration of tool 10 and the optical elements). This permits adjusting the operation of the system for the particular tool 30 and tip 40 used, more particularly, for automatically adjusting operation in the event that the tool and/or tip is changed during a procedure. The information element 42 can include a resistor coding or a more complicated memory device, such as PROM or bar code. The information element 42 also can include calibration data relating to the optical and physical operating characteristics of the tip 40, as already described, and other information such as the age of the tip or the number of times the tip has been used (or hours of use). The latter information can provide that a tip can be discarded (or not used until inspected) when its predicted useful life has been reached. In cases when both a tip information element 42 and a tool information element 32 are used, it is preferred that the stored calibration information not be redundant.

Figure 4A:
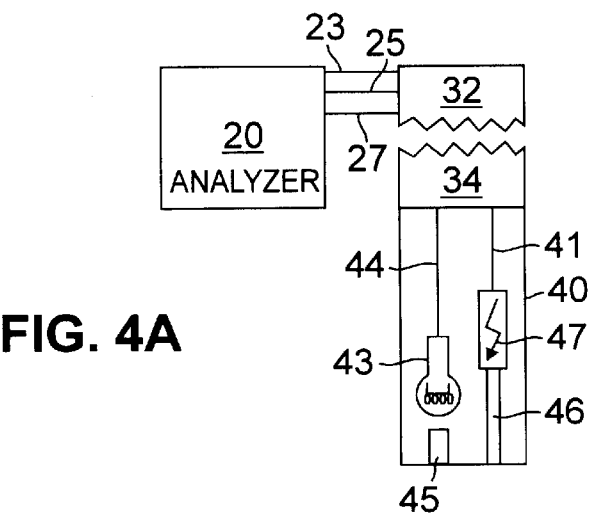
FIGS. 4A–4C are illustrations of various embodiments of the optical emitting and detecting elements for use in the interrogator tool of FIG. 1.
Figure 4B:
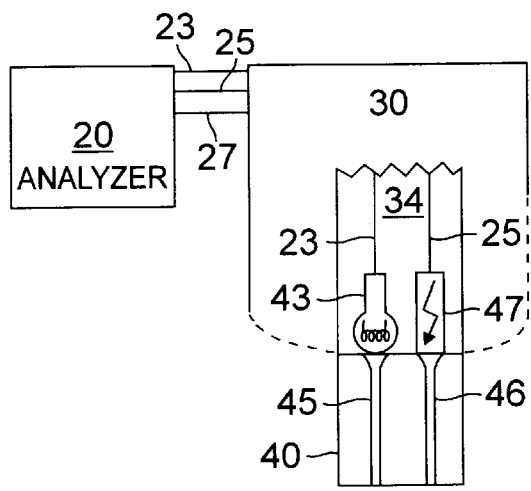
Figure 4C:
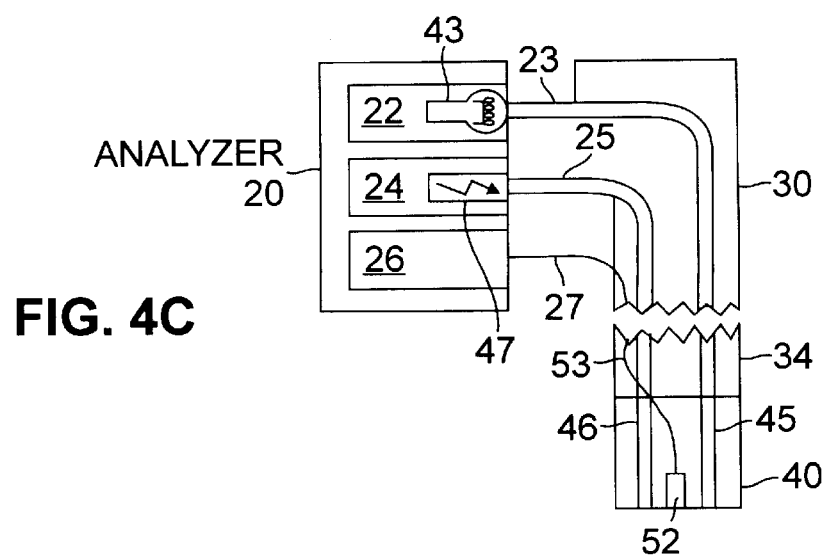

Referring now to FIGS. 4A–4C, three variations of the arrangement of the optical elements for emitting and detecting light are now described, without any implied limitation to these specific arrangements. Referring to FIG. 4A, in one embodiment of tip 40, tip 40 includes a broadband filament light source 43, which is electrically coupled to light source controller 22 by signal path 23 passing to and through tool 30 and signal path 44 in tip 40, and a light detector 47, such as a photodetector (e.g., a phototransistor, photodiode, charge coupled device (CCD), etc.), which is electrically connected to spectrometer 24 by signal path 25 in tool 30 and signal path 41 in tip 40. Light source 43 has an optical window 45 to couple light from source 43 and launch it into tissue, and light detector 47 has an optical window 46 to couple light at the distal end of tip 40 and transmit it to detector 47, through wavelength selective filters (not shown in FIGS. 4A–4C). Optical windows 45 and 46 may be glass or plastic inserts, or portions of fiber optic guides or some other optically transmissive material (e.g., an epoxy). As an example, photodetector 47 may include four discrete photodetectors, each having a wavelength selective filter interposed to filter the coupled light. In this illustrative example, four electric signals corresponding to the four wavelengths of the spectra characteristics are transmitted to spectrometer 24 on path 25. More or fewer photodetectors and filters could be used.

In a different structure, in which the light source is a plurality of discrete wavelength LED's mounted in tip 40 as light source 43 to launch multiplexed lights into tissue, the aforementioned multi-element photodetector arrangement could be used when there is a frequency multiplexed system, and a single photodetector could be used when there is a synchronous multiplexing system. Other variations are believed apparent to those skilled in the art, subject to space and cost considerations in constructing tip 40.

With reference to FIG. 4B, in an alternate embodiment, light source 43 and photodetector 47 may be located in tool 30, shown secured at the distal end 34. In this case, the optical windows in tip 40 extend completely therethrough to couple light between the light source and the light launching window and between the light coupling window and the light detector. In this embodiment, the tool calibration information 36 would account for the optical calibration characteristics of the detector 47, or in analyzer 20 (FIG. 4C), e.g., in spectrometer 24. Preferably, the photodetector 47 is disposed in the distal end of shaft 34 so that the mechanical interconnection couples the fiber optic guides 45 and 46 of tip 40 to the light source 43 and photodetector 47, whereby the photodetector 47 passes an output signal corresponding to the detected light to spectrometer 24 on signal path 25, and the light source 43 is controlled by signal path 23. Alternately, the light source 43 and photodetector 47 could be located elsewhere in tool 30, and coupled to the distal end 34 by suitable fiber optic waveguides (not shown).

With reference to FIG. 4C, in another alternative embodiment, the light source 43 is included in analyzer 20, e.g., as part of controller 22, and the light detector 47 is included in analyzer 20, e.g., as part of spectrometer 24, such that the light emitted and sensed are coupled between analyzer 20 and tool 30 over fiber optic signal paths 23 and 25, which mate with corresponding fiber optic elements 45 and 46 of tip 40, respectively.

Of course, it should be understood that variations of the foregoing embodiments are deemed within the scope of the present invention. For example, in one useful embodiment, the light source 43 is a broadband filament light source located in tip 40 and electrically coupled to light source control 22 by wire signal paths 23 and 45, and the light detector 47 is located in analyzer 20, e.g., as a functional part of spectrometer 24, with the light coupled at tip 40 passed to detector 47 over fiber optic guides 46 and 25. In this case, as noted but not shown, the light detector 47 can be easily constructed to detect multiple selected discrete frequencies, by use of filters, gratings and other frequency selective optical elements. This facilitates use of frequency selective demodulation of sensed broadband light. Rotating wavelength selective filters and a single photodetector or a plurality of photodetectors with fixed wavelength selective filters could be used as a matter of design choice. This embodiment avoids the need to minimize the size and weight of the photodetecting equipment, which are more important concerns for tool 30 and tip 40. For another example, the light source 43 can be located in tool 30, and the photodetector 47 located in analyzer 20, so that the calibration information of tool 30 includes the light source, and the light source can be replaced if necessary, during a surgical intervention with minimal risk to the patient. For yet another example, one or both of the fiber optic elements 45 and 46 can be secured to the exterior surface of the end effector tip 401, for example, by a suitable adhesive, or in the form of a sleeve that the end effector tip 40 is passed into, such that the sleeve maintains the fibers 45 or 46 in a predetermined orientation relative to the tip 40 during use, once the sleeve is securely in place. Optionally, such a sleeve may be a body-compatible plastic (or a wrapping of suitable tape or a heat shrink material) that also serves to seal the coupling between tip 40 and the distal end 30 of tool 30, e.g., against wicking of body fluids which might interfere with an optical connection. Other variations are believed to be within the scope of the present invention.

Referring to FIG. 4C, a temperature sensor 52 optionally is included in tip 40 and operatively connected to acquire and pass temperature related information to analyzer 20, e.g., over signal path 53 and signal path 27. It should be understood that this temperature sensor can be included in any tip 40. In the case that the temperature sensor is a near infrared based detection system, or other such light-based system, then the element shown as 52 could instead be an appropriate light emitting source, provided that the light detector 47 is modified to detect the appropriate wavelength from which the temperature information can be derived (in the conventional manner for such temperature monitoring systems). Indeed, the appropriate light illumination for the temperature sensing may be incorporated into the light source 43, or a second light source (not shown) may be included and multiplexed (by frequency or synchronously) with the light related to sensing spectral characteristics.

Thus, in one implementation, the analyzer 20 and tool 30 are constructed as rugged, reusable devices having relatively long useful lives, and the detachable tip 40 can be constructed as either durable reusable devices, or consumable devices having a more limited useful life.

In a preferred embodiment, the foregoing interrogation tool 10 operates as follows. The tissue is illuminated by a broadband light source located in tip 40. Some of the irradiating light is reflected, some is absorbed, and some is transmitted. There also may be some fluorescence. The light passing through the tissue is coupled into tip 40 and the particular spectral characteristics of a selected number of wavelengths of interest are then sensed. As is well known, the relative values of transmitted and absorbed light vary as a function of tissue type, composition, and histology, tissue thickness, and the wavelength of light. This permits discriminating tissue types and structures based on difference in the transmission spectra.

Referring to FIG. 2, an example of transmission spectra determined for four different tissue types are shown. These spectra are actual data collected by an experimental prototype bi-valve grasping tool, similar to that shown in FIG. 3, operating on tissue in-vivo in a living animal undergoing laporoscopic surgical intervention under an approved animal-study protocol. The tissue types illustrated are bile duct A, ureter B, artery C, and vein D. It is noted that the transmission spectra for these tissue types are clearly distinct from one another. Importantly, as the inventors have realized, although the precise spectra for a given tissue type will vary from one person to the next, and from one tool analysis location to another, a set of spectra can be selected which permit a wide variation from person to person, such that the different transmission spectra ranges for the different tissue types are sufficiently and clearly distinct. This enables the interrogation tool 10 of the present invention to discriminate and identify many different major tissue types, and in particular those tissue types and structures that are likely to lead to problematic complications if improperly subjected to the surgical intervention.

In this regard, a library of such tissue types can be empirically created based on selected transmission spectra. The term "detection spectra" is used interchangeably herein with the term "transmission spectra". The former is believed to be a more accurate descriptor, and the latter is used to indicate that the radiation has been transmitted through the tissue to be characterized. Classification algorithms also can be established using well-known analysis techniques, such as K-Nearest Neighbors (KNN) or Soft Independent Modeling of Class Analogy (SIMCA). Once the system has acquired the transmission (detection) spectra for the tissue interrogated, the acquired data is then processed using one or more of these algorithms, and the library of spectra records, and the interrogated tissue type can be determined within acceptable confidence limits or identified as not identifiable. The number of data points used to define a transmission spectra for a given tissue type may vary from one type of tissue to another, and depending on the sun to another, depending on the surgical intervention to be performed. In addition, the number of data points can vary depending on the computing power of analyzer 20, which often is a result of a cost-benefit decision, and is thus deemed to be matter of design choice.

As will become apparent to a person of ordinary skill in the art, the library of tissue types can include a set of spectra records corresponding to distinct types of tissue classes, including, for example, ureter, liver, kidney and other types such as those listed in FIGS. 11A and B. The library also can include a set of spectra records corresponding to different pathological states of a selected tissue class, such as normal, precancerous, and cancerous states of a given tissue class, e.g., pancreas, liver, lung, or more than one given tissue. The library also could include a set of spectra records corresponding to a sequence of effects of a surgical intervention on a given tissue type, for example, on a blood carrying tissue. In this example, and without limitation, the intervention is electrocautery of normal blood flow in tissue, and representative pathological states include normal blood flow in the tissue, coagulated blood in the tissue, over-coagulated blood in the tissue, and char, wherein the blood carrying tissue contains at least one of an artery, a vein, and a capillary bed. Of course, these different sets can be combined in the same library, or in different libraries, such that the surgical procedure being performed determines which library or which parts of a library are to be used.

Preferably, the library includes a plurality of predetermined spectra records corresponding to the plurality of known tissue types. It also is possible to provide for modifying the library by inputting data from a remote source, such as, for example, a CD-ROM, a magnetic tape, an IC ROM, a modem, a PCMCIA disk, a PCMCIA memory, a direct user input, and a previously obtained detection spectra.

In an optional preferred embodiment, the signal processor further is configured to improve its accuracy of identification in response to continued operation of the signal processor in using classification algorithm to identify a detection spectra. Thus, it is desirable to have a determination memory wherein at least some data is stored in response to each tissue characterization. Then, the classification algorithm can be used to average multiple ones of detection spectras over time, to improve the accuracy of the first output signal. Further, the classification algorithm also can be used to provide an output signal corresponding to a probabilistic strength of the first output signal. This provides a confidence factor for the surgeon to continue with the surgical procedure or take additional detection spectra.

It also should be understood that the classification algorithm is able to provide an output signal or signals corresponding to multiple tissue types being identified.

Regarding the spectrometer, it is preferably operable to detect a feature of the detection spectra, i.e., the detected electromagnetic radiation, selected from at least one of absorbance, scattering, fluorescence, optical rotation, elastic scattering, temperature, time resolved optical data, frequency resolved optical data, reflectance, opacity and turbidity. More specifically, the spectrometer is configured to separate an absorbance effect and a scattering effect of the electromagnetic radiation. This will permit one or more of performing a time-resolved analysis, a frequency-resolved analysis, and a multifiber spatial-resolved analysis (using multiple fibers and/or multiple detections covering the space to be analyzed).

The optical sensor components can be built into a tip 40 of any configuration, from flat to cylindrical, single member tips to multi-member tips. In a single member tip, the light source and detector may be mounted side by side on a planar surface with parallel optical axes that are perpendicular (normal) to the tissue contacting surface (see FIGS. 4A–4C). This would form a reflective mode sensor. Another reflective mode sensor is configured with light source and detector on diametrically opposed surfaces, pointing away from each other (see FIG. 3B). Yet another reflective mode sensor is configured with the light source and detector (or the corresponding fiber optic windows) on the same surface with the optical axes at an angle to each other, to minimize light passing directly from the emitter to the detector without passing through tissue (see FIG. 3G). In addition, the reflective mode and transmissive mode sensor may be combined on a single instrument by integrating multiple light source/detectors or fiber optic elements. Also, multiple sets or arrays of emitter and detector windows can be provided (see FIG. 3C). This is particularly useful for tools having multiple functions, such as electrocautery cutting using a thin edge or wires, and electrocautery coagulation using a broad edge (not shown).

Figure 5:
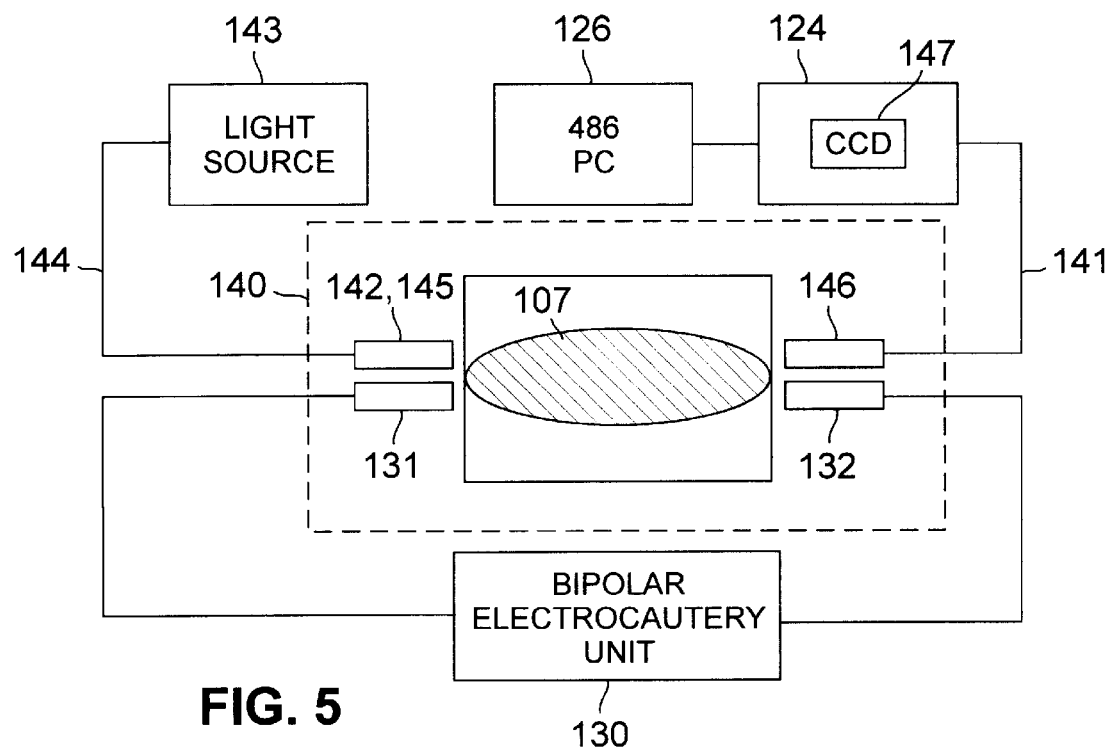
FIG. 5 illustrates a schematic block diagram of an interrogator tool apparatus in accordance with an embodiment of the present invention.

With reference to FIG. 5, an apparatus representative of a smart surgical tool in accordance with the present invention includes an electrocautery end effector function and a tissue monitoring function. The latter includes a light emitting window 145 and a light detecting window 146, placed in opposite surfaces of a bivalve tip 140 for grasping a sample tissue 107. A light source 143, preferably a broadband light source, such as a filament lamp located in tool 30 is coupled to emitting window 145 by an optical fiber guide 144. A commercial bipolar electrocautery unit 130, e.g., model Force B available from ValleyLabs, Inc. was used to pass current through electrical contacts 131 and 132 disposed on opposite sides of tissue sample 107. Spectroscopic data obtained via fiber optic 141 coupling window 146 to detector 147 was collected by a CCD spectrophotometer 124, which incorporates detector 147, in this case Ocean Optics model SD-1000, and the collected data was provided to a signal processor 126, in this case a Intel model 80486-DX66-microprocessor based system. Processor 126 is used to record spectra from tissue 107 at discrete wavelengths ranging between 400 nm and 1100 nm in 1024 channels, with one spectrum recorded every 25 ms.

Such data can be processed in multiple ways. For example, a class analysis can be performed (Haaland, 1989) that would allow use of such data to generate a model for determining which selected spectra fall into each of the tissue types to be discriminated. The exact mathematical model used is not important, provided only that a series of spectral characteristics can be identified that allow automated calibration of the identification method.

Advantageously, the present invention provides a smart surgical tool that can perform a tissue heating function, using tips for electrocautery, thermally regulated heating and laser based heating, and control the heating function to inhibit intervention in the presence of tissue identified as inappropriate.

The present invention also is applicable to controlling bleeding during a surgical intervention. Generally, two conditions must be satisfied for tissue to bleed: 1) There must be a hole in a blood vessel, and 2) there must be blood flow. It is known that some form of tissue welding can be used for closing a hole or for stopping the normal blood flow. Further, when preparing a tissue for surgical removal, it is necessary to shut off blood supply to the tissue. This is traditionally done with sutures, though suturing is time-consuming, can rupture tissues and cause bleeding itself, and can be a focus of infection. Thus, alternative methods of closing blood vessels are being sought, such as electrocautery and thermally heated hemostatic devices. If done properly, using the right time, current, and pressure, larger vessels can be seared together, preventing bleeding during tissue removal. Further, such a sealed site will heal correctly because the tissue that is left will form a strong scar. This approach can also be used to tack down tissue using spot-welds, and even to reseal open compartments, such as blood vessels.

It requires much skill and experience for a surgeon to make the proper assessment between too little, too much, and just the right amount of electric current or heat by the look and feel of the tissue.

In the context of the present invention, spectroscopic or optical methods are used to detect either the loss of a spectral signal related to the presence of hemoglobin (e.g., the blood has been destroyed in the vessel) or that the flow has stopped or that the hole is cauterized or otherwise closed. Accordingly, the present invention provides an semi- or fully-automated tissue interrogation tool system to determine tissue doneness based on spectroscopic analysis, for assessment and control of progress during an electrocautery or thermal intervention.

Figure 6:
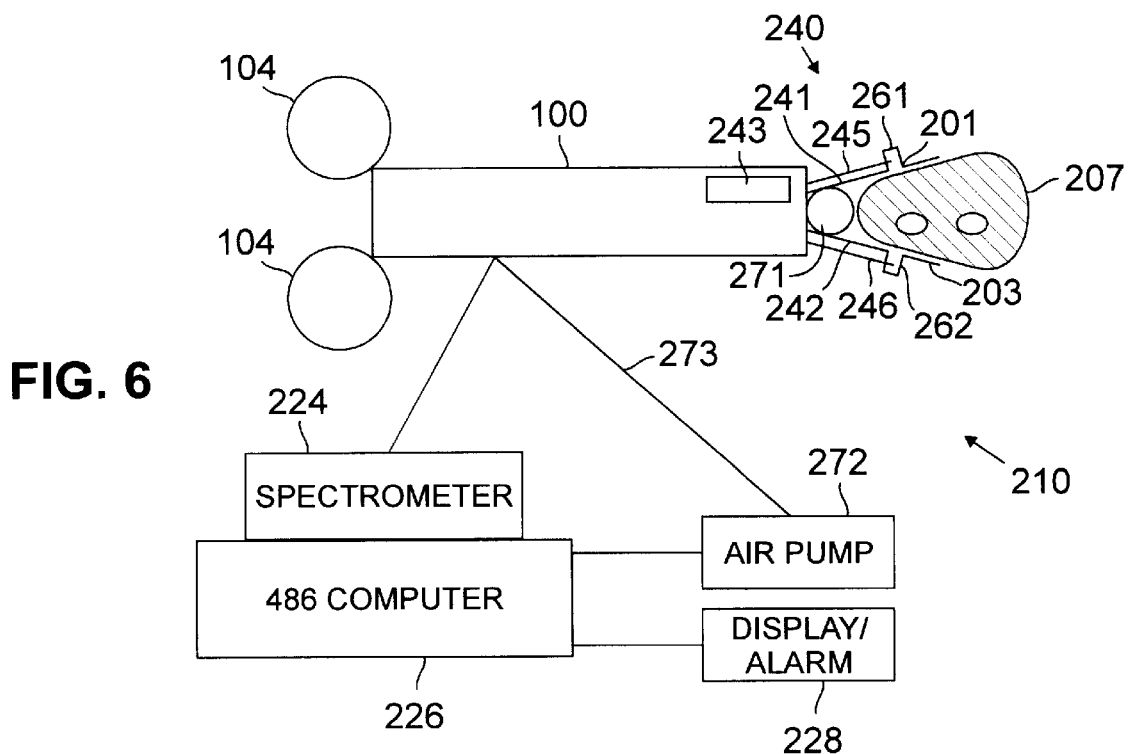
FIG. 6 illustrates a schematic diagram of another embodiment of a surgical interrogation tool in accordance with the present invention.

With reference to FIG. 6, an embodiment of such a tool 210 having a tip 240 adapted for electrosurgery and tissue interrogation is shown. In tool 210 tip 240, a current passes between a pair of grasper members 201 and 203 which are opposed jaws having respective electrocautery jaws 241 and 242. Jaws 241 and 242 pass current to heat tissue 207 interposed between members 201 and 203. Optical fibers 245 and 246 are disposed to terminate in mirrored wells 261 and 262 located in the jaws, and launch and collect light in the wells. Optical elements (not shown) may be inserted in wells 261 and/or 262 to enhance coupling light between the tissue and the optical fibers. Fiber 245 is connected to light source 243 and fiber 246 is connected to spectrometer 224.

In operation, signal processor 226 sounds a first alarm (audibly sounded on display 228), to alert the surgeon that the tissue contains a significant blood vessel that must be sealed or cauterized (or some other tissue type that should be avoided). In the case of a blood vessel, the surgeon can initiate a first intervention by heating the tissue to coagulate the blood (or both). The processor 226 then sounds a second alarm that instructs the surgeon that the coagulation is complete, e.g., based on detecting the disappearance of the spectral characteristics corresponding to blood flow or the appearance of the spectral characteristics corresponding to coagulated blood. Then the surgeon can sever the tissue and proceed with the intervention as appropriate. Signal processor 226 includes a microprocessor chip, for example, model 486DX66 based computer or similar or equivalent device, having additional functionality for generating alarms when one or more predetermined criteria are met (or exceeded). Optionally, signal processor 226 also controls the delivery of electrocautery current through grasper members 201 and 203 in response to the change in spectral characteristics of the tissue corresponding to the coagulation of blood. The surgeon can change tips, if necessary, to sever the tissue, perhaps hemostatically, and monitor possible blood flow such that hemostasis can be applied to coagulate any blood flow found.

The present invention provides both advantageous and surprising results. First, most surgeons use unipolar instruments that direct current from the tip of the electric knife through the body to a grounding plate electrode, commonly placed under the patient. When they use such a device, large amounts of current pass through tissue that is not meant to be cut or seared, and searing small or large areas risks collateral damage. An advantageous technique for tissue welding or searing, known as bipolar electrocautery, can be used that instead directs current between two tongs (or relatively closely positioned electrodes) of the device, e.g., as shown in FIG. 3A, 3E, 3I and 3J, thus sparing at least some of the nearby tissue from electric current. However, most surgeons do not use such a device and are not familiar with the potential use as a tool for controlling injury. Second, most surgeons are trained that one should not use electrocautery on large vessels, such as arteries larger than 5 mm in diameter and veins larger than 3 mm in diameter (arteries are easier to close off as their thick muscular wall sears nicely, but veins are harder as they have thin walls that do not close off so easily). Thus, the surgeons who utilize electrocautery, even bipolar electrocautery, are actually taught away from using electrocautery to perform procedures such as tissue welding. Third, most surgeons estimate whether tissue is "cooked vs. burned" by eye and feel, even though such estimates may not be reliable. Further, most surgeons find the welding properties of electrocautery to be unpredictable, particularly if used in larger tissues areas and larger blood vessels. Many who have observed electrocautery welding technique see e.g. Camran Nezhat et al., "Operative Laparoscopy (Minimally Invasive Surgery): State of the Art", *Journal of Gynecological Surgery*, Volume 8, Number 3, 1992, still find it difficult to control tissue welding. Thus, the skill barrier that must be crossed in order to perform this technique is effectively prohibitively high. This is particularly important during minimally-invasive surgery performed using an endoscope-type instrument (e.g., surgery performed through a periscope-like tube without opening up the patient). If a portion of tissue, such as an artery, is improperly or not fully coagulated, or is not identified and inadvertently (or accidentally) severed, this tissue will bleed profusely when cut, and may force emergency surgery (due to the blood loss and its attendant risks, as well as the fact that blood will block the endoscopic field of view, preventing further surgery via the endoscope in some cases). At the very least, such bleeding leads to worsening of scarring, and lengthening of surgery; at the worst, such bleeding can be a life-threatening complication of surgery.

The present invention advantageously overcomes these problems by automatically monitoring the tissue state and determining whether such blood vessels are present or adequately coagulated, in real time, even as electric current is passed through tissue between bipolar tong electrodes.

The specific triggering event used by a smart surgical tool in accordance with the invention could vary, but could include such measures as the disappearance of spectral signal corresponding to the presence of blood, or a class-analysis approach that searches for a color signature associated with properly browned tissue, or both. Similarly, char has a spectral signature that is different than tissue, whether based upon absorbance or scattering, or both. As mentioned before, time-resolved methods, frequency resolved methods, or spatially-resolved methods can separate absorbance from scatter, and allow an individual analysis of wavelength-dependent absorbance and wavelength-dependent scattering. Such an analysis may yield additional information, or for cost-effectiveness or other competitive reason, such a time-resolved, frequency-resolved, or space-resolved measurement may be avoided as well.

In any event one of these selected characteristics can be used as a boundary for the safe operating condition. For example, a bipolar electrosurgical cutting tool in accordance with the invention could shut down when an artery is fully baked, and there is minimal danger of bleeding if the tissue is subsequently cut. This would prevent overcooking, which can cause bleeding well after surgery due to improper healing, as well as undercooking, which will lead to immediate bleeding when the tissue is cut by the surgeon.

It has been recognized by the inventors that tissue in which arterial blood is flowing demonstrates a well-known pulsatility of signal. As tissue is thermally coagulated by a bipolar device, or even a unipolar probe exerting pressure on the tissue, this signal disappears. Next, as the pressure of the device is removed, the venous blood will flow back into the tissue.

In accordance with an aspect of the present invention, a spectroscopic method can be used to detect the flow of blood back into the tissue, demonstrating the patency of the venous system. Thus, spectroscopy can be used to verify if the blood flow has been adequately destroyed for intervention.

One manner of implementing such a system is to provide a tool having optical fibers disposed in the probe to monitor the tissue proximate to the probe. The presence of pulsatility and/or capillary refill when pressure exerted by the tool is removed could allow identification of the point at which blood flow no longer occurs in the tissue. In this regard, with reference to FIG. 6, the tool 210 includes a pneumatic system such as an air bladder 271 to open and close controllably grasper jaws 241 and 242, or to close the jaws and then release some pressure and then reapply pressure, allowing blood to refill the tissue at times. This change can detected by spectrometer 224, and the absence of spectral change as the pressure is modulated can be used to determine the time at which occlusion has occurred, and an alarm needs to sound. The opening and closing effect can be achieved by having air bladder 271 inflated by a pump 272 and hose 273, using positive pressure or negative pressure under operative control of processor 226. An alternate structure could use a conventional cable operated grasping tool to apply the pressure variations. Other structures could easily be considered for such use and are omitted without exclusion. When the pulsating response is not desired, the air bladder 271 illustrated in FIG. 6 and related structure could be omitted from the tool and end effector tip.

Another embodiment of the invention provides a tissue interrogating tool including a penetrating device with an optical sensor for use in determining whether or not the penetrating device has penetrated to the desired body cavity. The puncturing tool may be, for example, a trocar or surgical insufflation needle coupled with such an optical sensor. The optical sensor may have a multiplicity of optical components at the distal end of the puncturing tool for emitting and launching light and coupling and detecting light to provide a signal corresponding to the spectral characteristics of the tissue presented to the tool. Thus, this tool is able to generate an alarm when penetration into a desired tissue type has occurred or penetration into an undesired tissue type is about to occur and/or has occurred.

It should be understood that the light emitting window element and the light detecting window element may be arranged in any configuration on the tip so that, in response to the light intensity launched by the light emitting window, the light detector produces a signal that corresponds to the spectral characteristics of the tissue being interrogated. In this regard, the light emitting and detecting window elements may be oriented on the tool, in either (1) transmissive line of sight, wherein there is a line of sight light path between the light emitting window and the light detecting window and the presence of tissue reduces the intensity of light illumination sensed by the detecting element, (2) transmissive over the horizon, wherein there is no direct line of sight light path between the light emitting and detecting windows, the presence of tissue couples light to the light detecting window, and the absence of tissue reduces the intensity of light illumination coupled to the light detecting window, (3) reflective over the horizon, wherein there is no direct line of sight light path between the light detecting and light emitting window, the presence of tissue attenuates the light intensity sensed at the light detecting window and the absence of tissue results in an increased light intensity sensed at the light detecting window, or (4) some combination thereof.

When multiple discrete wavelengths of light are used, the selected wavelengths may be launched and the desired wavelengths, which may be different from the wavelengths launched, sensed using wavelengths multiplexed by frequency or by time for transmission to the tissue on one common optical waveguide. This permits using a single fiber optic, having a very small diameter, as the light emitting element (i.e., the optical window). Alternately, the discrete wavelengths may be separately delivered over corresponding dedicated optical waveguides. Further, more than one fiber optic waveguide may be used to deliver the same wavelength(s) simultaneously at different points on the device tip.

Similarly, the light detecting window may be one optical waveguide adapted to receive all light sensed, which detected light signal can be optically (frequency) or electrically (time) demultiplexed and separated into different sensed light intensity signals corresponding to the different desired wavelengths. Alternately, the light detecting window may have separate optical waveguides for receiving the light and either selectively passing one discrete wavelength to a light detector or passing the light to a wavelength selective light detector, for generating the separate corresponding electrical signals. Further, the light detecting window may have more than one optical waveguide to detect the light such that the detected light signals are averaged, summed, or otherwise related to yield a detected light level for each emitted frequency.

Preferably, the light emitting and detecting windows comprise a plurality of optical components, such as optical fibers, at the device tip which are plugged into and thus coupled to an optical bench containing the light source(s) and the light detector(s) such as photodiodes, phototransistors, photomultiplier tubes, charge coupled devices, and the like. Such optical fibers can be made of glass or plastic materials for reusable and disposable device tips. Glass fibers are preferred for reusable tips and plastic fibers are preferred for disposable tips. The optical bench can be made in a durable case in the surgical tool or the analyzer and reused for both disposable and reusable device tips. The optical fibers may be identical in construction and symmetrically secured in or to the tissue penetrating device tip so that either fiber (or group of fibers) may be used either to illuminate tissue or to couple light from the tissue. Alternatively dedicated male and female interconnections can be used for coupling the emitter to the emitter window and the detector to the detector window. As discussed, the optical bench can be in the tip, the tool, or in the analyzer, and it can be separated into one bench for emitting light and another bench for sensing light, each being independently located in one of the analyzer, tool, or tip, as desired in the particular application.

Advantageously, the present invention provides for a tissue intervention tool having tips with optical elements and control circuits that can be used to determine reliably and accurately the tissue type being or to be penetrated. It also provides for disposable components for trocars or surgical insufflation needles containing inexpensive optical elements to insure optimal performance of the invention and prevention of cross-contamination between patients. Alternately, the invention provides durable trocars and insufflation needles with optical elements that will withstand sterilization by autoclave, gas, and x-ray sterilization techniques.

Referring now to FIGS. 7A–7D, in this embodiment tip 40 is illustrated as a conventional trocar tip for laparoscopic surgery, which has been modified as described below. The sheath and obturator tubes are not shown. The optical elements are provided in the form of first and second lengths of optical fibers 745 and 746, and an optical coupler 790 connecting the tip 40 fiber 745 to a light source 43 for launching one or more of the selected illuminating wavelengths or a broadband light source as the case may be, onto fiber 745 and a light detector 47 for sensing light coupled at tip 40 by fiber 746. In this embodiment, light source 43 and detector 47 are part of an optical bench located in tool 30 (see FIG. 4B), and are not shown in FIGS. 7A–7D.

In this embodiment, the conventional surgical trocar appliance (reusable or disposable) is modified by the incorporation of two optical fibers 745 and 746 into or on the structure. Optical fibers 745 and 746 are each a single fiber that is small in diameter and may be of conventional plastic or glass construction. The fiber diameter could be selected to be from between 0.05 and 0.25 mm, but should be selected such that the mechanical function of the appliance tip 40 is not compromised. Fibers 1.0 mm diameter or larger may be used on large trocar applications, i.e., a trocar having a 10.0 mm diameter. Glass optical fibers currently have superior optical transmission characteristics and are available in the smaller sizes. Glass optical fibers also have better mechanical and thermal properties, such as the ability to withstand autoclave temperatures, although high-temperature plastics are being introduced and are expected to be useful in the present invention. Glass fibers also have a benefit in that they can act as an electrically isolating spacer between conductive elements such as are used in electrocautery applications discussed above. Plastic fibers are much less expensive, which makes them well suited to disposable devices and reusable devices where sterilization by autoclave is not required.

Referring to FIGS. 7A–7D, in this embodiment the optical fibers 745 and 746 are secured to tip 40 by being mounted into small holes formed in the tip 40 near the point of the tip and fixed in place with a medical grade adhesive or potting compound. The exact positions of the ends of fibers 745 and 746 are preferably chosen to minimize the likelihood of a direct optical path between the two, which would allow optical crosstalk. The position of the fiber ends in the cutting faces of tip 40 also are selected so that when the light illumination changes in response to the ends of fibers passing into different types of tissue and/or body cavities to acquire the spectral characteristics.

One suitable position is to have the elements 745 and 746 geometrically symmetrical, so that the optical transmission/reception characteristics of the fibers are identical and even interchangeable. This permits making coupler 790, in which the fibers terminate (see FIG. 7E) a durable component that is plug-compatible with the optical bench, having secured optical fibers 745 and 746. Alternately, coupler 790 may have a "plug" that is keyed so that a selected optical element will be used for sensing (element 746) (or illuminating) (element 745) light, but not both. This is useful when an optical element, or its manner of mounting or its positioning, is specially designed for light illumination or sensing, but not both.

In addition, tip 40 and coupler 790 may be constructed with a coding system as described above to have a code that identifies the type of tip, i.e., its surgical end effector structure and the configuration of optical elements 745 and 746. This code is read by analyzer 20, for example, when tip 40 is coupled to the distal end 34 of tool 30 and/or when the device is turned on. The code is identified and can be used to select appropriate timing signals and signal levels for controlling the illumination and detection of light, and to select appropriate thresholds for processing the sensed light signals and making determinations regarding tissue spectral characteristics. In this embodiment, analyzer 20 may be provided with a memory device (not shown) containing a conventional look-up table of prerecorded information, for providing all of the necessary operating parameters that are associated with a given code. Further, if a code is not recognized, the device may automatically shut down so that incompatible appliances are not incorrectly used. Any method of coding tips 40 may be used, such as using selected resistor values or digital words in an integral circuit appliance 10 and corresponding contacts in coupler 790 for electrically sensing the code by analyzer 20. In addition, product labeling such as a bar code and a photodetector array and sensors may be used for optically sensing the code by analyzer 20. Coding optical sensing devices are discussed in, for example, U.S. Pat. Nos. 4,621,643, 4,700,708, and 4,770,179, the disclosures of which are hereby incorporated by reference.

Referring again to FIGS. 7A–7D one construction of trocar has a tip 40 that includes a 3-face pyramid. The faces are cut on essentially flat planes that intersect at an angle of 120° relative to each other (see angle α in FIG. 7B) and so that the midline of one facet and the edge of an adjacent facet form an angle of 45° (see angle β in FIG. 7C) with the apex being the point of tip 40. This trocar tip construction is conventional.

Figure 7A:
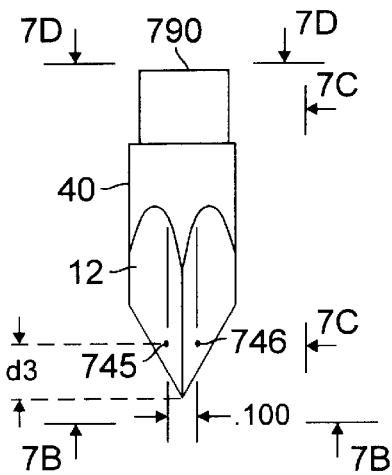
FIG. 7A is a front elevated view of a trocar tip tissue penetrating device in accordance with the present invention.
Figure 7B:
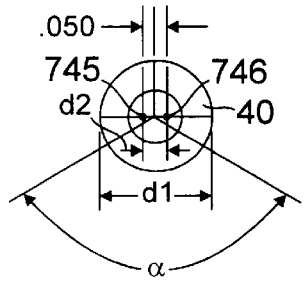
FIG. 7B is a tip end view taken along line 7B—7B of FIG. 7A.
Figure 7C:
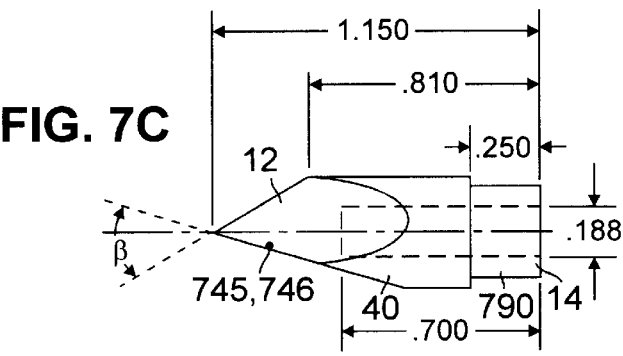
FIG. 7C is a side view taken along line 7C—7C of FIG. 7A.
Figure 7D:
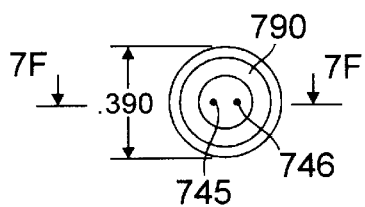
FIG. 7D is a base end view taken along line 7D—7D of FIG. 7A.

For a conventional trocar made of 440 stainless steel having an outer diameter d1 of 0.39 inches, fibers 745 and 746 are respectively inserted into two parallel 0.013-inch-diameter holes, which are spaced apart a distance d2 of 0.1 inches along a diameter of tip 40, and centered about the point of tip 40. In this embodiment, the faces of fibers 745 and 746 are flush with the plane of the facet of trocar tip 40, and terminate a distance d3 of 0.07 inches from the point of tip 40 as illustrated in FIG. 7A.

The trocar tip 40 may be constructed as follows. Two holes are drilled. The fibers 745 and 746 are coated with silicone adhesive and passed into the drilled holes so that the ends of fibers extend from the tip faces. The adhesive is allowed to set. The ends of fibers are then trimmed either separately or during the process for tipping the tip. The fiber ends are then polished. The inside of trocar tip 40 may be partially filled with a potting material to provide additional support for fibers 745 and 746.

Figure 7E:
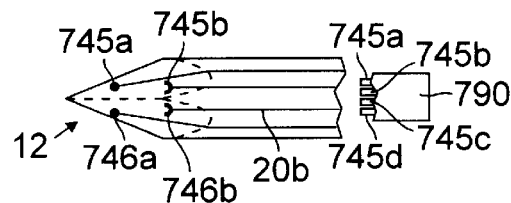
FIGS. 7E–7G are side sectional views of a trocar tip tissue penetrating device, taken along line 7F—7F of FIG. 7D, in accordance with different embodiments of the present invention.

Referring to FIG. 7E, an alternative construction of tip 40, is shown. In this embodiment, tip 40 has two pairs of optical elements 745 and 746 namely optical fibers 745a and 746a, and optical fibers 745b and 746b. The placement of the ends of fibers 745b and 746b are selected so that element 746b will couple predominantly light illumination launched by optical element 745b, rather than 745a. In one embodiment, the two pairs are separately operated to provide different signals of light (and dark) illumination corresponding to different sensing locations on tip 40. Pair of fibers 745a and 746a provide the light (and dark) illumination at the point of tip 40 and fibers 745b and 746b provide the light (and dark) illumination closer to the base of tip 40. This provides a first signal responsive to tissue spectral characteristics at the leading point of tip 40, and a second signal responsive to spectral characteristics at the base of tip 40.

In a second embodiment, the pairs of optical elements in FIG. 7E may be connected so that optical elements 745a and 745b are coupled to a common light source and optical elements 745a and 745b are coupled to a common light detector (not shown).

Figure 7F:
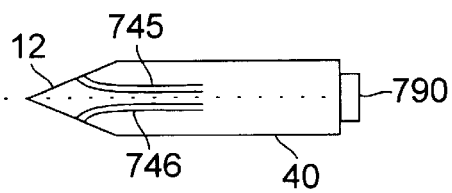
Figure 7G:
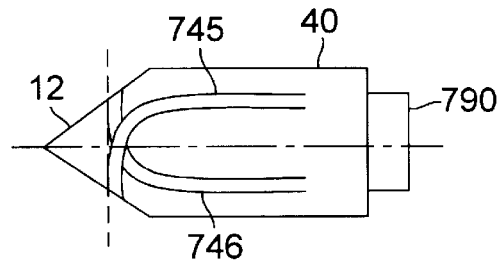

In alternate embodiments, the optical elements 745 and 746 may be constructed to terminate with their ends normal to the tissue contacting surface (see FIG. 7F) perpendicular to the longitudinal axis (see FIG. 7G), or various other angles or combinations of angles, taking into consideration the allowable radius of curvature of the optical fibers.

Figure 7H:
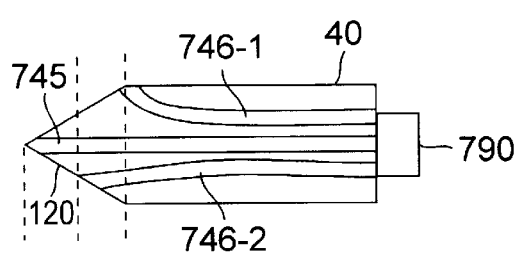
FIG. 7H is a cross sectional view of the tip of a trocar tip in accordance with an embodiment of the present invention.

Referring to FIG. 7H, yet another configuration of a trocar tip 40 could include a single optical fiber 745 passing along the axis of tip 40 and terminating with its end in the leading point of tip 40 (or proximate thereto), and using two light detecting fibers 746-1 and 746-2 to couple light illumination in response to the light emitted by fiber 745. Fibers 746-1 and 746-2 are shown as terminating at different distances from the point of tip 40 and on opposite sides of the axis of tip 42, thereby to provide different coupled light signals as described above. Thus, for a pyramid tipped trocar, the ends may terminate in different faces. Alternately, the ends may terminate on the same side of tip 40, e.g., in the same face of a pyramid tipped trocar tip. As used herein, unless otherwise specified, references to the optical elements being "at" the tissue contacting surface should be understood to refer to the end(s) of the optical fiber or the emitting surface of a light source being one of flush with the plane of the tissue contacting surface, a short distance below the plane, or a short distance above the plane, such that the end does not interfere with the mechanical function of the tissue contacting surface.

Referring to FIGS. 8A–8E, an elliptical tip 40 of a surgical appliance 10 that is a needle is shown. The ellipsoid is formed in a flat plane at a conventional angle Γ, for example, 15° relative to the longitudinal axis of needle tip 40. The optical elements 845 and 846 are secured along the minor axis of the ellipsoid plane, on a diameter of the needle tip 40, disposed in parallel to the longitudinal axis. The elements 845 and 846 are secured by being mounted to needle tip 40 by epoxy, e.g., Bipax brand optical grade epoxy available from Tra-Con, Milford, Mass. The ends of elements 845 and 846 are polished flush with the flat ellipsoid tip 40. A same construction applies to irrigation and suction probe tubes, which may have a cylindrical tip in a plane perpendicular to the longitudinal axis of the tube.

Figure 8A:
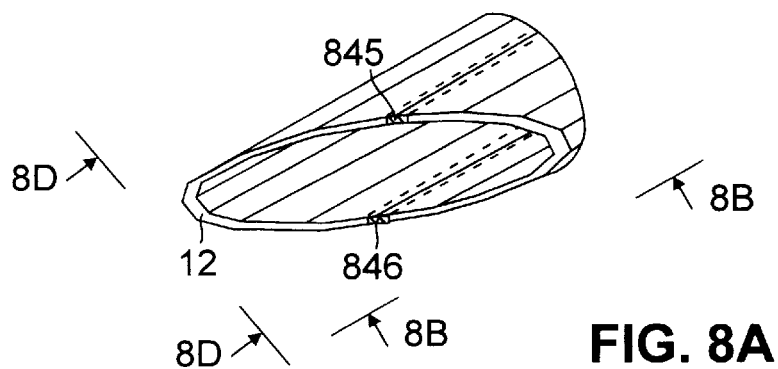
FIG. 8A is an elevated perspective view of the tip of an ellipsoid tipped needle-type tissue penetrating device in accordance with the present invention.
Figure 8B:
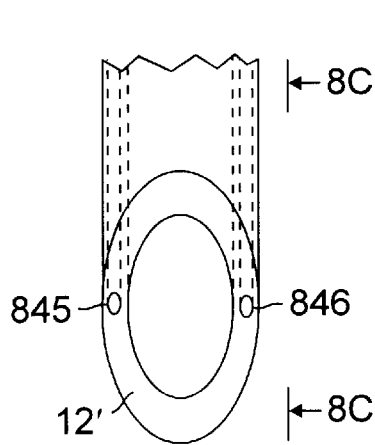
FIG. 8B is a front view of the tip of FIG. 8A taken along line 8B—8B.
Figure 8C:
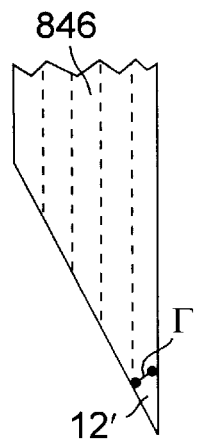
FIG. 8C is a side view taken along line 8C—8C of FIG. 8B.
Figure 8E:
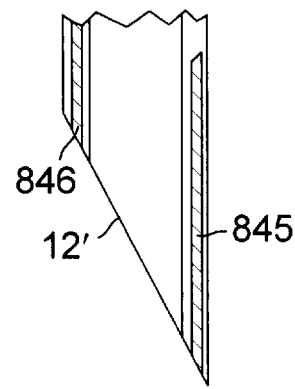
FIG. 8E is a side view of an alternate embodiment of the device tip of FIG. 8A.
Figure 8D:
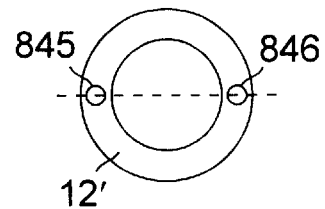
FIG. 8D is an end view taken along line 8D—8D of FIG. 8A.

The ends of optical fibers 845 and 846 are illustrated in FIGS. 8B and 8E as on a diameter of needle tip 40 and so that they will essentially enter the tissue at about the same time. Alternately, they could be disposed on a chord of appliance needle tip 40, e.g., in a plane perpendicular to the longitudinal axis or in a plane parallel to the tissue contacting face. Further, they may be oriented with one end (preferably the light emitting window) in the lead portion and the other end (preferably the light detecting window) in the trailing portion of the tissue contacting face as illustrated in FIG. 8E.

Alternatively, elements 845 and 846 may be secured to needle tip 40 by being wrapped inside a thin film of material, e.g., mylar. In addition, elements 845 and 846 in the form of optical fibers may be inserted into channels formed in the material of a tip 40 and sealed in place with an adhesive.

The ends of optical fibers 845 and 846, where they emerge from the surgical appliance 10 to be coplaner with the appliance tissue penetrating tip 40, must be polished. Polishing insures proper mechanical function of the tip and improves the optical coupling of the fibers. The fibers may be polished by the tip sharpening process or they may be polished after tipping by a secondary wet or dry process. When a coding system is employed for identifying appliance tips 40 and selecting operating parameters, the code is preferably provided at the junction where the appliance tip 40 is coupled to a tool 30, and the information is then provided to the analyzer 20. For example, with reference to the embodiment illustrated in FIG. 9, the code may be installed in coupler 990 and sensed by a corresponding code reading circuit in coupler 991 (not shown), whereas in an embodiment where fibers 945 and 946 terminate into coupler 991, the code may be provided in another manner and sensed by a corresponding code reading circuit appropriately.

Figure 9:
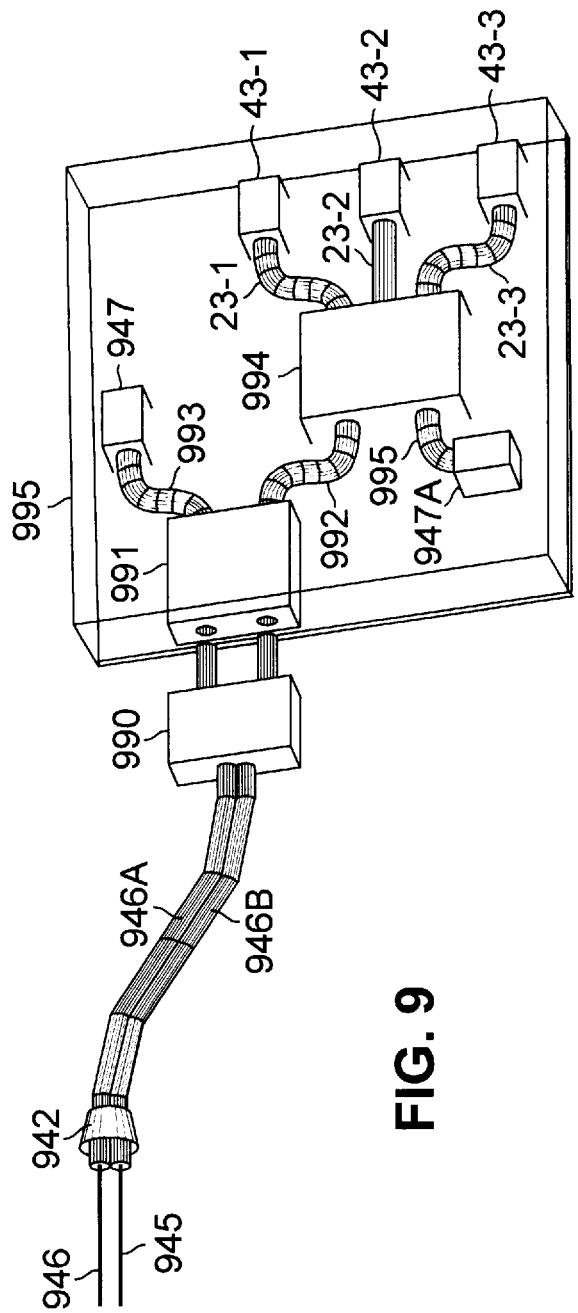
FIG. 9 is a schematic drawing of an embodiment of a synchronous multiplexed optical coupling system for the system of FIG. 1.

Referring now to FIG. 9, fiber optics 945 and 946 may fit into a coupler 995 which is an optics module (an optical bench) that transmits and receives monochromatic light over optic fibers at n different wavelengths to and from tip 40, where n is greater than or equal to one. It has a bulkhead mounted, duplex connector (female) 991 which mates with the male connector 990 at the end of tip 40 or alternatively with the ends of optical fibers 945 and 946. Fibers 946 and 945 are also illustrated as jacketed fibers 946A and 946B and incorporate strain relief 942 as appropriate. One optical fiber, or channel, illustrated as channel 992 in FIG. 9, is configured as a transmission channel, and the other channel, illustrated as channel 993 in FIG. 9, is configured as the reception channel. These channels are typically made of the same commercial fiber optic material.

There are at least two methods of combining n different wavelengths and coupling them into an optical fiber, e.g., channel 992, namely synchronous or time multiplexing and wavelength or frequency multiplexing. Any combination technique may be used.

For synchronous multiplexing, different monochromatic light sources 43-N are provided of which three are illustrated as light sources 43-1, 43-2, and 43-3. Light sources 43-N are preferably light emitting diodes (LEDs), although semiconductor lasers or broadband light sources (e.g., filament bulbs) combined with wavelength selective filters also may be used or combinations thereof, e.g., one broadband light source, and one infrared LED with one ultraviolet source (for fluorescent applications). Hence, when a broadband light source is used without wavelength filtering, it is to be understood that fibers 945 and 946 typically will carry light that is other than monochromatic light. The term monochromatic also should be understood to allow some variation of wavelength within a small bandwidth.

The light sources 43-N are energized according to timing control signals. Preferably, the timing of the operation of light sources 43-N and detector 947 provide for illuminating only one light source 43-N at a time, according to a selected sequence. Any suitable timing control signals sequence may be used. The light sources 43-N are respectively connected by fiber pigtails 23-N (i.e., 23-1, 23-2 and 23-3) to an optical coupler 994 such as model #P92-7019-241-1 manufactured by AMP/Kaptron, Harrisburg, Pa. When necessary, optical elements such as lenses may be used to couple light into an optical fiber or to couple light from a fiber to a light detector.

Coupler 994 is a 2×3 coupler which combines the light provided at each of the input fibers 23-N in a symmetric homogeneous fashion and passes it along to each of the two output channels. One output channel is the transmission channel 992 of connector 991. The other output fiber optic channel, channel 995, is directed to a photodetector 947A, preferably a photodiode such as model #BPX66 manufactured by Siemens Components, Inc., Cupertino, Calif. Detector 947A provides an electrical signal corresponding to the intensity of light emitted by each source 43-N. This is used to monitor and/or control the illumination level to avoid intensity drift and to maintain uniform illumination from pulse to pulse of each wavelength.

Reception channel 993 of connector 991 connects the sensed light from tip 40 and a second light detector 947, preferably a photodiode. Detector 947 provides an electrical signal corresponding to the intensity of light sensed at tip 40 of the surgical tool 30 (for each monochromatic source 43-N in this embodiment). This light includes the light reflected by tissue 107 in response to the illumination by each source 43-N. When desired, it may include tissue fluorescence wavelengths.

Figure 10:
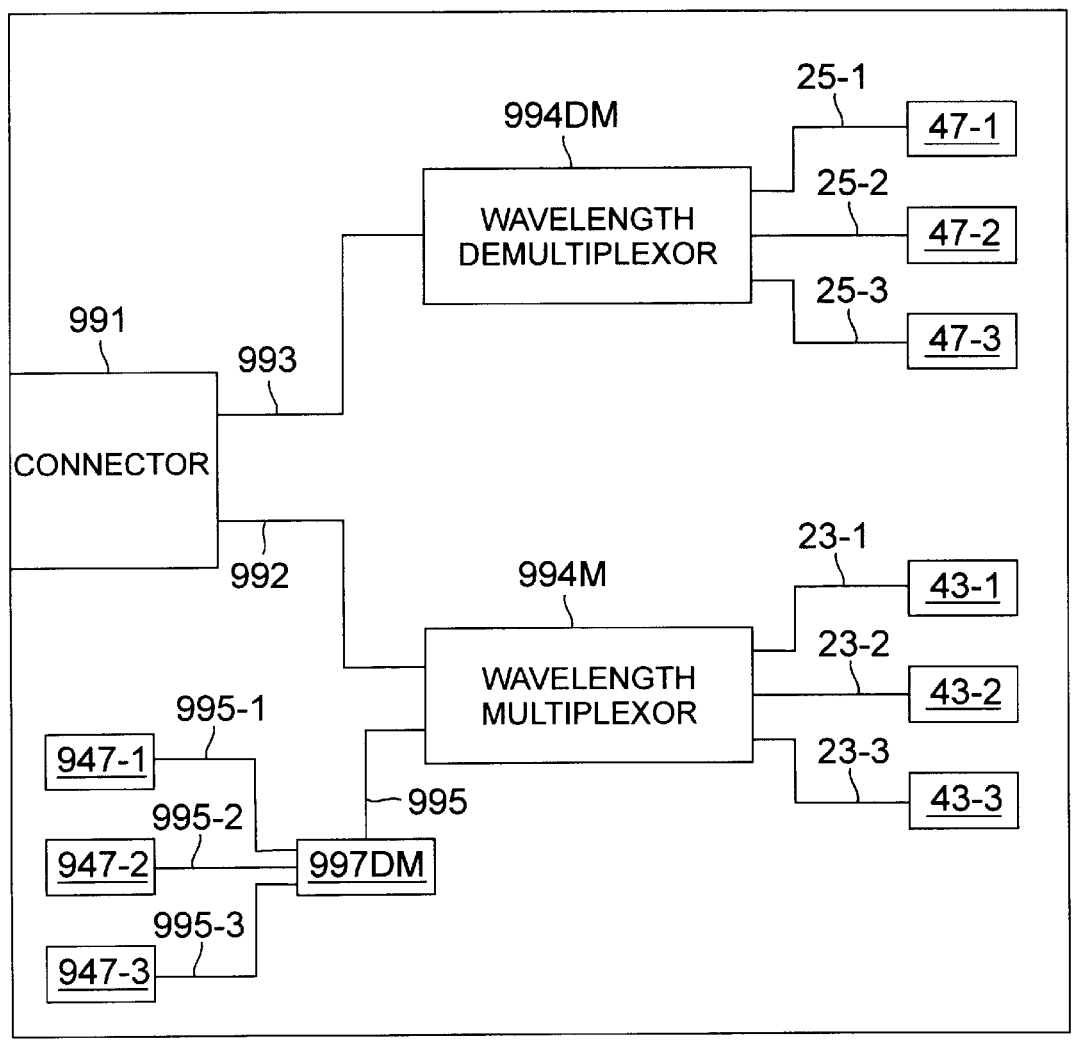
FIG. 10 is a schematic drawing of an embodiment of a wavelength multiplexed optical coupler for the optical system of FIG. 1.

Referring to FIG. 10, a wavelength multiplexing scheme is shown. In this design, separate photodetectors 47-N and 947-N are provided for each of the n wavelengths emitted by sources 43-N. The light from each of sources 43-N is launched into fiber pigtails 23-N, which combine in a wavelength multiplexing coupler 994M, such as models #99100-3 or 99103-3 available from AMP, Inc., Harrisburg, Pa. The output fiber of coupler 994M is routed to the transmission channel 992 of the bulkhead connector 991. Coupler 994M has the same characteristic of combining light in a symmetric, homogeneous fashion as 2×3 coupler 994 illustrated in FIG. 9.

The reception channel 993 of the bulkhead connector 990 is directed to a wavelength demultiplexing coupler 994DM, such as models # 99100-3 or 99103-3 available from AMP, Inc. Each output pigtail 25-N of demultiplexer 994DM, which contains one wavelength signal N is routed to an individual light detector 47-N (photodiodes are preferred). Similarly, a second output of coupler 994M is passed on fiber 995 to a second wavelength demultiplexing coupler 997DM, and then by pigtails 995-N to detectors 947-N. This scheme provides n discrete detectors 947-N to monitor sensed light and dark illumination at sources 43-N and n discrete detectors 47-N to monitor sensed light and dark illumination at tissue 107 at tip 40 of surgical appliance 10. No additional electronic signal multiplexing or conditioning is required.

In this wavelength multiplexing embodiment, the timing function is much simpler because each light source may be illuminated simultaneously. Hence, a single square wave denoting on and off states is adequate. The dark illumination may be sampled during each off state, following the aforementioned delay.

The same light source drive circuit and photodetector preamplifier may be used for both the synchronous and frequency multiplexer systems, except that the photodetector preamplifier must be repeated for each of the photodetectors in the frequency multiplexer system. The synchronous multiplexing technique uses fewer optical and detector components than the wavelength, but it requires additional electronic switching and processing.

It should be understood that any one of the various structures for the optical elements shown in FIGS. 3, 3A–3J, 4A–4C, 7A–7H and 8A–8E as described herein may be applied in a straightforward manner to the other various structures of tip 40 including those not described herein, which variations are believed to be within the ability of a person skilled in the art.

It also should be understood that in the case that the light source is a broadband light source, such as a filament bulb mounted inside or on tip 40, the sensed light signals are best demultiplexed by a spectrometer-detector system as previously described. The demultiplexing by frequency can be performed in the aforementioned manner. The demultiplexing by time can be performed using frequency selective filters that are periodically interposed between the sensed light and a photodetector, to chop the sensed light into frequency selective segments, which segments can be separated in time to acquire the desired spectral characteristics.

Lastly, it is to be understood that time-resolved, frequency-resolved, or spatially-resolved methods can be used to extract additional information, in an analogous manner, which information can be used to generate similar tissue identifications. Modification of the foregoing to include one or more of the time/frequency/space resolved methods is believed to be within the abilities of a person of ordinary skill in the art, once knowledgeable about the present invention, and, therefore, within the scope of the invention.

Another optical sensing embodiment can be implemented without any surgical tool at all. In this method, the entire surgical field is illuminated by broadband energy. A camera captures an image of the field which is stored as pixels in a memory array. Various narrow band filters can be sequentially interposed between the camera and the resulting sequence of monochromatic images stored in page memory arrays. The paged memory can be analyzed by a computer to yield colorimetric information about each pixel of the image. The colorimetric information can be further analyzed for spectral fingerprints of various tissue qualities, e.g., blood vessels or ureters. Pixels which match the spectral fingerprint would be highlighted on a video system, perhaps by brightness control or flashing or labelling with a cursor.

Advantageously, the present invention also is applicable to surgery where it is important to differentiate between normal and abnormal types of tissue, as well as different types of tissue. Examples include the following:

1) Differentiation of physiological lumens

The interrogatory tool of the present invention includes probes which can identify blood vessels (arterial and venous), as well as bile ducts and other lumens such as ureters, nerves, fallopian tubes, etc., from surrounding tissue. The colorimetry technique already described can be used for this tissue type analysis and identification. This application minimizes the likelihood of severing the bile duct, for example, which is a frequent complication requiring traditional surgical intervention, and/or cutting through the ureter, which is also a frequent type of injury.

2) Determination of cautery status

Bipolar electrocautery is often used to control locally and separate blood vessels. In accordance with the present invention, optical elements can be incorporated into the bipolar electrodes. For example, the optical fibers could be sandwiched in an array between electrodes of a unipolar device or mounted on or adjacent electrodes of bipolar devices in a transmissive or reflective configuration. The optical elements can locate blood vessels as well as determine the coagulation status of the tissue by measuring the absolute transmission spectra and/or the color change over time and detecting any formation of char, by its spectral signature, at the tissue interface. The color change may be relative to a baseline measurement or a preselected spectral criteria corresponding to a good quality coagulation. This real time information is useful to the clinician, who can use it to adjust electrocautery parameters, such as power level and duration. The information also can be used for automatic parameter control.

The same optical sensing technology also may be used for observing and controlling unipolar electrosurgical cautery, laser cautery, and laser welding of tissues.

3) Safety stapler

Staples or clips are routinely used in place of sutures. Occasionally, the staples are misplaced so that they obstruct or damage an underlying structure. For example, a blood vessel may be inadvertently occluded or a nerve may be accidentally severed after being "caught" in the jaws of a stapler. Alternately, an underlying structure may be situated in an unusual location and be caught unknowingly. The optical sensor of the present invention can be incorporated into the jaws of a stapler or clip applier to interrogate the tissue to be stapled or clipped. Advantageously, an alarm can be sounded if there is important tissue trapped between the jaws (e.g., blood vessel or nerve) or if the tissue cannot be reliably classified as only the desired tissue free of undesired structures. The alarm also could be configured as a safety interlock which prevents the stapler from actuating during an alarm condition (unless the alarm is overridden). As already noted, a plastic light conducting staple can be utilized in the light detection path to monitor the effectiveness of the closure.

4) Diseased tissue identification:

Endometriosis is often distributed throughout the surgical field. The colorimetry technique can be used to identify areas of endometriosis. For example, the spectral characteristics of normal tissue and the endometriosis can be ascertained, and the two or more characteristics can be used to decide whether the tissue being interrogated is normal or abnormal. Further, in combination with the cautery status indicator, the optical sensing technology of the present invention can be used to determine when the endometriosis has been effectively removed.

In bowel surgery, an optical probe can be similarly used to identify obstructions or inflamed tissue beds. Similarly, in cancer surgery, where it is important to identify and remove multiple areas of tumor tissue growing in the body cavity without removing healthy normal tissue, a pathological tissue classification can be used to distinguish cancerous tissue from noncancerous and other types of healthy tissue. In this respect, the invention also overcomes the problems of the direct biopsy techniques.

EXAMPLE

Referring to FIGS. 2, 3A, 3B and 11, a preliminary study on a live pig was conducted using a grasper tool similar to FIGS. 3, 3A and a suction irrigator probe tool similar to FIG. 4C. Sixty-three sets of data were obtained in a laparoscopic procedure using the aforementioned Ocean Optics Spectrometer, which was known to be faulty and in need of service, and with vacuum leaks in the prototype tooling which made sustained insufflation difficult. The prototype system included a conventional fiber optic light source supplied by Wolff of West Germany and a fiber optic Spectrometer model PSD 1000 supplied by Ocean Optics, Inc., Dunedin, Fla. The light source fiber and detector fiber were mounted on opposing jaws of a Kleppinger style Bipolar forceps, also supplied by Wolff. The jaws of the Kleppinger forceps are typically 1 mm wide and 12 mm long. The suction irrigator and grasper tools are thus preferably sized so that they will fit through the lumen of a 5 mm canula. The suction irrigator should have a large internal lumen (4.5 mm) to preserve its primary function.

Each set of data includes a spectral measurement every one nm in the range of 400 to 1100 nm (although only four such spectra are illustrated in FIG. 2 for clarity of presentation). A library was empirically constructed for each of the categories listed on FIG. 11A and B: Abdominal Wall Fat, Liver, Gall Bladder, Bowel, Bladder, Ureter, Uterine Wall, Diaphragm, Small Bowel, Colon Fat, Artery, Vein, Ganglia, Bony Pelvis, and Bile Duct. An analysis was conducted using KNN and the predictive algorithm has a 76% success rate. Of sixty-two determinations, with the prototype equipment, there were a total of 15 false position and false negative determinations. These are reported in FIG. 11 where the number of successful determination are on the diagonal, and the false determinations are indicated above or below the diagonal, for the various tools and tissue types in the study.

One skilled in the art will appreciate that the present invention can be practiced by other than the described embodiments, which are presented for purposes of illustration and not of limitation.

We claim:

1. Apparatus for non-destructive interrogation of tissue comprising:
   a minimally invasive surgical tool end effector;
   a first element positioned at the end effector to launch one or more discrete wavelengths of radiation into a tissue to be interrogated;
   a second element positioned at the end effector to couple light launched from the first element that has passed through the tissue to be interrogated;
   a photodetector operatively coupled to said second element having an output of electrical signals corresponding to at least a portion of the light coupled by the second element; and
   a processor having an input for receiving said output of electrical signals, the processor being responsive to said output of electrical signals to determine non-destructively at least one characteristic of the tissue to be interrogated.

2. The apparatus of claim 1 wherein at least one of said first element and said second element further comprises a tissue contacting surface.

3. The apparatus of claim 1 wherein said end effector further comprises means for performing a surgical intervention.

4. The apparatus of claim 3 wherein at least one of said first element and said second element further comprises a tissue contacting surface.

5. The apparatus of claim 1 wherein the surgical tool end effector further comprises a bi-valve member having a first lever and a second lever and a hinge connecting the first and second levers together, and a tissue contacting surface containing at least one of the first and second elements.

6. The apparatus of claim 5 wherein the processor further comprises means for identifying a component of the electrical signals corresponding to pulsatile blood flow in the tissue being interrogated.

7. The apparatus of claim 6 further comprising an annunciator operable to generate an alarm in response to an identified pulsatile blood flow.

8. The apparatus of claim 6 in which the identifying means operates to identify a loss of pulsatile blood flow and to generate an alarm in response to said identified loss of pulsatile blood flow.

9. The apparatus of claim 5 wherein the bi-valve member is a forceps.

10. The apparatus of claim 5 wherein the first and second levers further comprise first and second edges operative to sever tissue therebetween and the tissue contacting surface containing at least one of the first and second elements further comprises a first tissue contacting surface at one of the first and second edges and a second tissue contacting surface at the other of the first and second tissue contacting surface, the first tissue contacting surface containing one of the first and second elements and the second tissue contacting surface containing the other of the first and second elements.

11. The apparatus of claim 10 wherein the processor further comprises means for identifying a component of the electrical signals corresponding to pulsatile blood flow in the tissue being interrogated.

12. The apparatus of claim 11 further comprising an annunciator operable to generate an alarm in response to an identified pulsatile blood flow.

13. The apparatus of claim 11 wherein the identifying means operates to identify a loss of pulsatile blood flow and to generate an alarm in response to said identified loss of blood flow.

14. The apparatus of claim 10 wherein the bi-valve member is an electrosurgical cutting instrument.

15. The apparatus of claim 10 wherein the bi-valve member is a hemostatic cutting instrument.

16. The apparatus of claim 10 wherein the bi-valve member is a forceps.

17. The apparatus of claim 1 wherein the surgical tool end effector further comprises a bi-valve member having a first member and a second member and the first and second members further comprise respective first and second edges to sever tissue therebetween, wherein at least one of the first and second elements is disposed proximate to one of the first and second edges.

18. The apparatus of claim 17 wherein the bi-valve member is an electrosurgical cutting instrument.

19. The apparatus of claim 17 wherein the bi-valve member is a hemostatic cutting instrument.

20. The apparatus of claim 17 wherein the bi-valve member is a scissors.

21. The apparatus of claim 1 wherein the surgical tool end effector further comprises a member having a first body and a second body, the first body having a first tissue contacting surface and the second body having a second tissue contacting surface, the first tissue contacting surface containing at least one of the first and second elements and the other of the first and second elements being contained on one of the first and second tissue contacting surfaces.

22. The apparatus of claim 21 wherein the processor further comprises means for identifying a component of the electrical signals corresponding to pulsatile blood flow in the tissue being interrogated.

23. The apparatus of claim 22 further comprising an annunciator operable to generate an alarm in response to an identified pulsatile blood flow.

24. The apparatus of claim 22 wherein the identifying means operates to identify a loss of pulsatile blood flow and to generate an alarm in response to said identified loss of blood flow.

25. The apparatus of claim 21 wherein the member further comprises a forceps.

26. The apparatus of claim 21 wherein the member further comprises a clamp.

27. The apparatus of claim 21 wherein the member further comprises a tissue cutting instrument.

28. The apparatus of claim 21 wherein the member further comprises a hollow fluid channel extending therethrough.

29. The apparatus of claim 1 wherein the member further comprises a tissue penetrating instrument.

30. The apparatus of claims 2, 4, 5, 6, 10, 11, 21, 22, 28 or 29 wherein the tissue contacting surface further comprises a sensor for determining the temperature of the tissue to be interrogated.

31. The apparatus of claim 30 further comprising a library of stored electrical signal components corresponding to a set of spectral records representative of a plurality of tissue types, wherein the processor is further operable to compare the electrical signals to at least one of the stored electrical signal components and identify the characteristic tissue type of the tissue to be interrogated based on a correlation between the stored electrical signal components and the electrical signals and the determined sensed temperature.

32. The apparatus of any of claims, 1, 5, 17, 6, 10, 11, 21, 22, 28 or 29 further comprising a library of stored electrical signal components corresponding to a set of spectral records representative of a plurality of tissue types, wherein the processor is operable to compare the electrical signal components and identify the characteristic tissue of the tissue to be interrogated based on a correlation between the stored electrical signal components and the electrical signals.

33. The apparatus of claim 32 wherein said library further comprises a set of spectral records corresponding to a plurality of distinct tissue types including ureter, liver and kidney.

34. The apparatus of claim 32 wherein said library further comprises a set of spectral records corresponding to different pathological states of a known tissue class including normal and cancerous states.

35. The apparatus of claim 32 wherein said library further comprises a set of spectral records corresponding to different effects of a surgical intervention on a blood carrying tissue including normal blood flow in said tissue, coagulated blood in said tissue and over-coagulated in said tissue, wherein said tissue is carrying one of an artery, a vein, and a capillary bed.

36. A method for non-destructively interrogating tissue comprising:
providing a surgical tool end effector with a tissue contacting surface, a first element coupled to a source of radiation and a second element coupled to a photodetector, positioning at least one of the first and second elements in said tissue contacting surface, and placing said end effector proximate to a tissue to be interrogated;
launching from the first element one or more discrete wavelengths of radiation into the tissue to be interrogated;
passing at least a first portion of said launched radiation through said tissue and coupling at the second element radiation that has been modified by passing through said tissue;
detecting the coupled radiation at the photodetector and producing an output of electrical signals corresponding to at least a portion of the detected radiation; and
processing the electrical signals to determine non-destructively at least one characteristic of the tissue to be interrogated.

37. The method of claim 36 wherein providing said end effector further comprises providing a tissue contacting surface and positioning at least one of the first and second elements in said surface.

38. The apparatus of claim 36 wherein providing said end effector further comprises providing an end effector for performing a surgical intervention.

39. The method of claim 38 wherein providing said end effector further comprises providing a tissue contacting surface and positioning at least one of said first and second elements on said tissue contacting surface.

40. The method of claim 39 wherein providing the surgical tool end effector further comprises providing a bi-valve member having a first lever and a second lever and connecting the first and second levers together, wherein one of the first and second levers contains the at least one of the first and second elements.

41. The method of claim 40 wherein the processing step further comprises identifying a component of the electrical signals corresponding to a pulsatile blood flow in the tissue being interrogated.

42. The method of claim 41 further comprising generating an alarm in response to an identified pulsatile blood flow.

43. The method of claim 41 in which the identifying step further comprises identifying a loss of pulsatile blood flow and generating an alarm in response to an identified loss of pulsatile blood flow.

44. The method of claim 36 wherein providing the surgical tool end effector further comprises providing a first body having a first tissue contacting surface and a second body having a second tissue contacting surface, and positioning at least one of the first and second elements on the first tissue contacting surface and positioning the other of the first and second elements on one of the first and second tissue contacting surfaces.

45. The method of claim 44 wherein the processing step further comprises identifying a component of the electrical signals corresponding to a pulsatile blood flow in the tissue being interrogated.

46. The method of claim 45 further comprising generating an alarm in response to an identified pulsatile blood flow.

47. The apparatus of claim 45 wherein the identifying step further comprises identifying a loss of pulsatile blood flow and generating an alarm in response to an identified loss of blood flow.

48. The method of any of claims 36, 40, 41, 44 or 45 further comprising providing a library of stored electrical signal components corresponding to a set of spectral records representative of a plurality of tissue types, comparing the electrical signals to at least one of the stored electrical signal components, and identifying the characteristic tissue type of tissue to be interrogated based on a correlation between the stored electrical signal components and the electrical signals.

49. The method of claim 48 wherein providing said library further comprises providing a set of spectra records corresponding to a plurality of distinct tissue types including ureter, liver and kidney.

50. The method of claim 48 wherein providing said library further comprises providing a set of spectra records corresponding to different pathological states of a known tissue class including normal and cancerous states.

51. The method of claim 48 wherein providing said library further comprises providing a set of spectra records corresponding to different effects of a surgical intervention on a blood carrying tissue including normal blood flow in said tissue, coagulated blood in said tissue and over-coagulated in said tissue, wherein said tissue is carrying one of an artery, a vein, and a capillary bed.

52. The method of any of claims 36, 40, 41, 44 or 45 further comprising determining the temperature of the tissue to be interrogated.

53. The apparatus of claim 52 further comprising providing a library of stored electrical signal components corresponding to a set of spectral records representative of a plurality of tissue types, comparing the electrical signals to at least one of the stored electrical signal components, and identifying the characteristic tissue type of the tissue to be interrogated based on a correlation between the stored electrical signal components and the electrical signals and the determined sensed temperature.

\* \* \* \* \*

UNITED STATES PATENT AND TRADEMARK OFFICE
CERTIFICATE OF CORRECTION

PATENT NO. : 5,769,791
DATED : June 23, 1998
INVENTOR(S) : Benaron et al..

It is certified that error appears in the above-identified patent and that said Letters Patent is hereby corrected as shown below:

Column 15, line 50, after "and" delete "depending on the sun" and insert --from one application--;
Column 29, line 42, after "claim" delete "5" and insert --1--;
Column 29, line 17, delete "passed through the" and after "that has" insert --been modified by--.

Signed and Sealed this

Twenty-second Day of June, 1999

Attest:

Q. TODD DICKINSON

*Attesting Officer*    *Acting Commissioner of Patents and Trademarks*